United States Patent
Mudde et al.

(10) Patent No.: US 11,090,381 B2
(45) Date of Patent: Aug. 17, 2021

(54) COILED-COIL CONNECTOR

(71) Applicant: OncoQR ML GmbH, Vienna (AT)

(72) Inventors: Geert Mudde, Breitenfurt (AT); Jorge Sepulveda, Vienna (AT); Christopher Taus, Vienna (AT); Liesbeth Mudde-Boer, Breitenfurt (AT)

(73) Assignee: ONCOQR ML GMBH, Tullnerbach (AT)

( * ) Notice: Subject to any disclaimer, the term of this patent is extended or adjusted under 35 U.S.C. 154(b) by 0 days.

(21) Appl. No.: 15/754,562

(22) PCT Filed: Sep. 1, 2016

(86) PCT No.: PCT/EP2016/070590
§ 371 (c)(1),
(2) Date: Feb. 22, 2018

(87) PCT Pub. No.: WO2017/037158
PCT Pub. Date: Mar. 9, 2017

(65) Prior Publication Data
US 2018/0236065 A1    Aug. 23, 2018

(30) Foreign Application Priority Data
Sep. 1, 2015 (EP) ................................. 15183330

(51) Int. Cl.
| | | |
|---|---|---|
| A61K 39/395 | (2006.01) | |
| C07K 14/595 | (2006.01) | |
| C07K 14/735 | (2006.01) | |
| C07K 7/08 | (2006.01) | |
| A61K 39/00 | (2006.01) | |
| C07K 16/00 | (2006.01) | |
| C07K 14/705 | (2006.01) | |
| A61K 39/39 | (2006.01) | |
| C07K 16/28 | (2006.01) | |

(52) U.S. Cl.
CPC .......... *A61K 39/3955* (2013.01); *A61K 39/00* (2013.01); *A61K 39/0011* (2013.01); *A61K 39/39* (2013.01); *C07K 7/08* (2013.01); *C07K 14/595* (2013.01); *C07K 14/705* (2013.01); *C07K 14/70535* (2013.01); *C07K 16/00* (2013.01); *C07K 16/283* (2013.01); *A61K 2039/5158* (2013.01); *A61K 2039/55522* (2013.01); *A61K 2039/627* (2013.01); *C07K 2317/622* (2013.01); *C07K 2317/92* (2013.01); *C07K 2317/94* (2013.01); *C07K 2319/73* (2013.01)

(58) Field of Classification Search
None
See application file for complete search history.

(56) References Cited

U.S. PATENT DOCUMENTS

| | | | | |
|---|---|---|---|---|
| 2013/0251712 A1* | 9/2013 | Zwaagstra | ......... | A61K 47/6817 424/133.1 |
| 2015/0166610 A1 | 6/2015 | Baudoux et al. | | |

FOREIGN PATENT DOCUMENTS

| | | | | |
|---|---|---|---|---|
| JP | 2010536396 A | 12/2010 | | |
| JP | 2015521158 A | 7/2015 | | |
| WO | 94/29332 A1 | 12/1994 | | |
| WO | 2012071649 A1 | 7/2012 | | |
| WO | WO-2013025261 A2 * | 2/2013 | ........... | G01N 33/582 |
| WO | 2014/009209 A2 | 1/2014 | | |
| WO | 2014/187743 A1 | 11/2014 | | |
| WO | 2015/006736 A2 | 1/2015 | | |
| WO | 2015/018806 A1 | 2/2015 | | |

OTHER PUBLICATIONS

Oude Blenke et al. "Coiled coil interactions for the targeting of liposomes for nucleic acid delivery," Nanoscale, 2016,8, 8955-8965 (Year: 2016).*
Arndt et al, "Helix-stabilized Fv (hsFv) Antibody Fragments: Substituting the Constant Domains of a Fab Fragment for a Heterodimeric Coiled-coil Domain" 2001, J Mol. Biol. 312:221-228.
Boucher et al, "Epidermal Growth Factor Tethered through Coiled-Coil Interactions Induces Cell Surface Receptor Phosphorylation" 2009, Bioconjug.Chem.1569-1577.
Chao et al, "Use of a heterodimeric coiled-coil system for biosensor application and affinity purification"; 1998, J. Chromatogr.B Biomed. Sci.Appl. 715:307-329.
Harris, Reed J. "Processing of C-terminal lysine and arginine residues of proteins isolated from mammalian cell culture"; 1995, J.Chromatogr.A 705:129-134.
Litowski et al, "Designing Heterodimeric Two-stranded x-Helical Coiled-coils"; 2002, J. Biol. Chem. 277:37272-37279.
Richardson et al, "Amino Acid Preferences for Specific Locations at the Ends of x Helices"; Science 1988, 240:1648-1652.
Serrano et al, "x-Helix Stability in Proteins: Empirical Correlations Concemin Substitution of Side-chains at the N and C-caps and the Replacement of Alanine by Glycine or Serine at Solvent-exposed Surfaces"; Journal of Molecular Biology 1992, 227(2):544-559.

(Continued)

*Primary Examiner* — Christina Bradley
(74) *Attorney, Agent, or Firm* — Loza & Loza, LLP; Michael F. Fedrick

(57) ABSTRACT

A connector of a helical coiled coil-type structure connecting a first and a second molecule, wherein the first molecule comprises a peptidic first alpha-helix and the second molecule comprises a peptidic second alpha-helix, which second alpha-helix is coiled to the first alpha-helix. The first alpha-helix comprises a C-terminal region consisting of a repeat of an amino acid motif a-$x_1$ and the C-terminal motif a-$x_1$-$x_2$, or an N-terminal region consisting of a repeat of an amino acid motif $x_1$-a and the N-terminal motif $x_2$-$x_1$-a, where a is a motif sequence of 4-8 amino acids, $x_1$ is Lysine, and $x_2$ is an extension of the motif. The extension consists of 1-10 amino acids and does not comprise more than 4 consecutive amino acids incorporated in said motif a-$x_1$ or $x_1$-a. In a multimeric protein, two polypeptide chains can be connected to each other by such connector.

17 Claims, 5 Drawing Sheets

Figure 5:
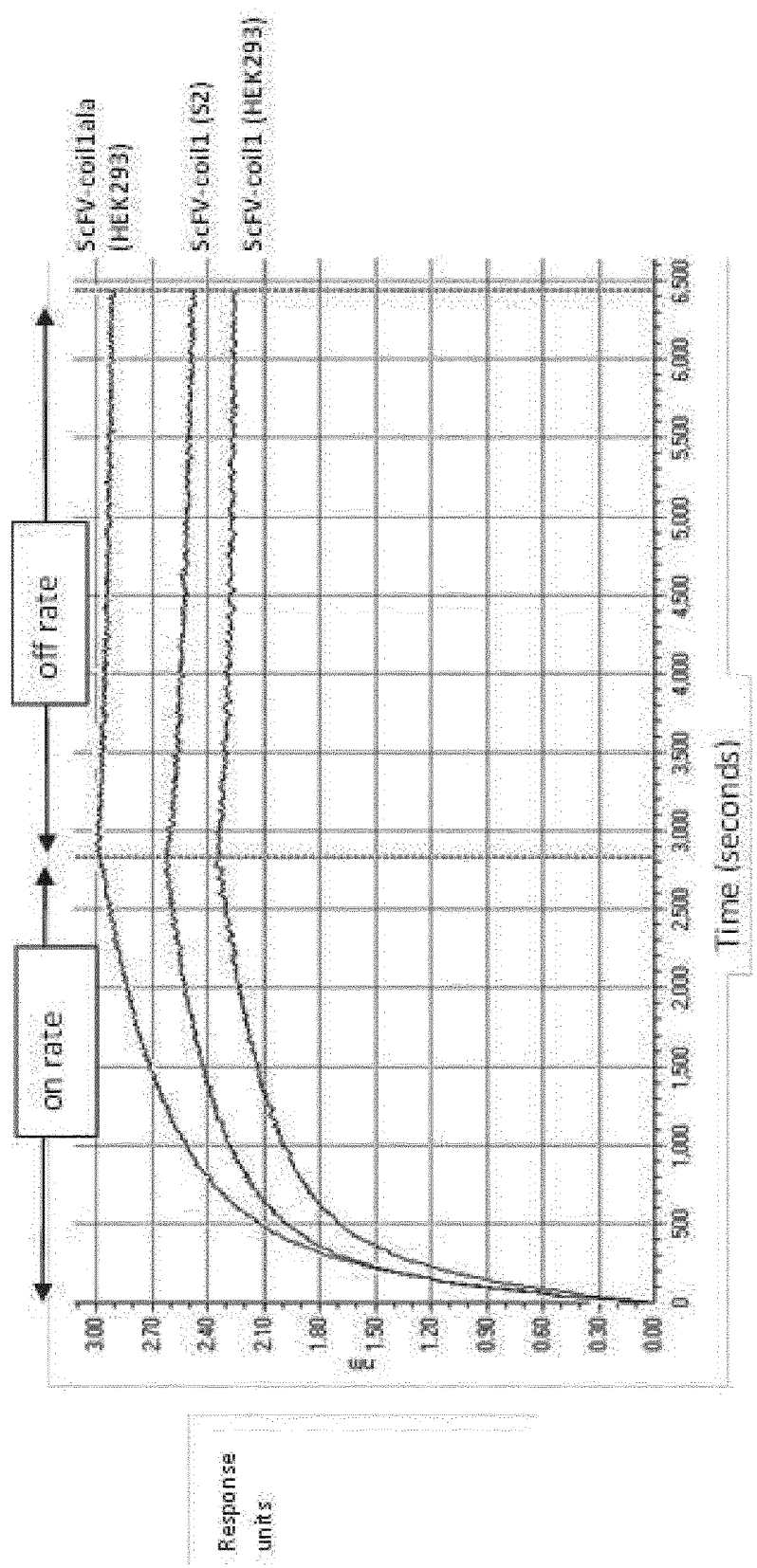

Specification includes a Sequence Listing.

(56) References Cited

OTHER PUBLICATIONS

Stuart et al, Isolation and Expression of cDNA Clones Encoding a Human Receptor for IgC (FcyRII); J. Exp. Med., Dec. 1987; 166: 1668-1684.
International Search Report for PCT/EP16/70590 dated Nov. 3, 2016; 7 pages.
Written Opinion for PCT/EP16/70590 dated Nov. 3, 2016; 6 pages.
Extended European Search Report for EP Application No. 1518330.8 dated Nov. 23, 2015; 8 pages.
Reinhardt et al., Rapid Covalent Fluorescence Labeling of Membrane Proteins in Live Cells via Coiled-Coil Templated Acyl Transfer, Bioconjugate Chemistry, 2015, vol. 26, pp. 2106-2117.
English translation of Japanese Office Action for Japanese Application No. 2018-512321, dated Aug. 7, 2020, 5 pages.

* cited by examiner

Fig. 1

SEQ ID 49

```
1          10         20         30         40         50
EVQLQQSGPE LKKPGETVKI SCKASGYTFT NYGMNWVKQA PGKGLKWMGW
51         60         70         80         90         100
LNTYTGESIY PDDFKGRFAF SSETSASTAY LQINNLKNED MATYFCARGD
101        110        120        130        140        150
YGYDDPLDYW GQGTSVTVSS GGGGSGGGGS GGGGSDIVMT QAAPSVPVTP
151        160        170        180        190        200
GESVSISCRS SKSLLHTNGN TYLHWFLQRP GQSPQLLIYR MSVLASGVPD
201        210        220        230        240        250
RFSGSGSGTA FTLSISRVEA EDVGVFYCMQ HLEYPLTFGA GTKLELKGGG
251        260        270        280        289
SKGP*EVSALE KEVSALEKEV SALEKEVSAL EKEVSALEK*
```

Underlined: VH and VL domains fused by a flexible linking sequence
Normal type set: flexible linker (maybe any linker)
In italics: pepE coil: 5 repeats of a heptad motif, C-terminal Lysine (italics and bold)

Fig. 2

SEQ ID 50

```
1          10         20         30         40         50
EVQLQQSGPE LKKPGETVKI SCKASGYTFT NYGMNWVKQA PGKGLKWMGW
51         60         70         80         90         100
LNTYTGESIY PDDFKGRFAF SSETSASTAY LQINNLKNED MATYFCARGD
101        110        120        130        140        150
YGYDDPLDYW GQGTSVTVSS GGGGSGGGGS GGGGSDIVMT QAAPSVPVTP
151        160        170        180        190        200
GESVSISCRS SKSLLHTNGN TYLHWFLQRP GQSPQLLIYR MSVLASGVPD
201        210        220        230        240        250
RFSGSGSGTA FTLSISRVEA EDVGVFYCMQ HLEYPLTFGA GTKLELKGGG
251        260        270        280        290
SKGP*EVSALE KEVSALEKEV SALEKEVSAL EKEVSALEKA
```

Underlined: VH and VL domains fused by a flexible linking sequence
Normal type set: flexible linker (maybe any linker)
In italics: pepE coil: 5 repeats of a heptad motif, C-terminal Alanine (italics and bold) as a C-terminal extension.

Fig. 3

SEQ ID 51

```
1          10         20         30    35
KVSALKEKVS ALKEKVSALK EKVSALKEKV SALKE
```

In italics: pepK coil: 5 repeats of a heptad motif, N-terminal Lysine (italics and bold)

Fig. 4
A
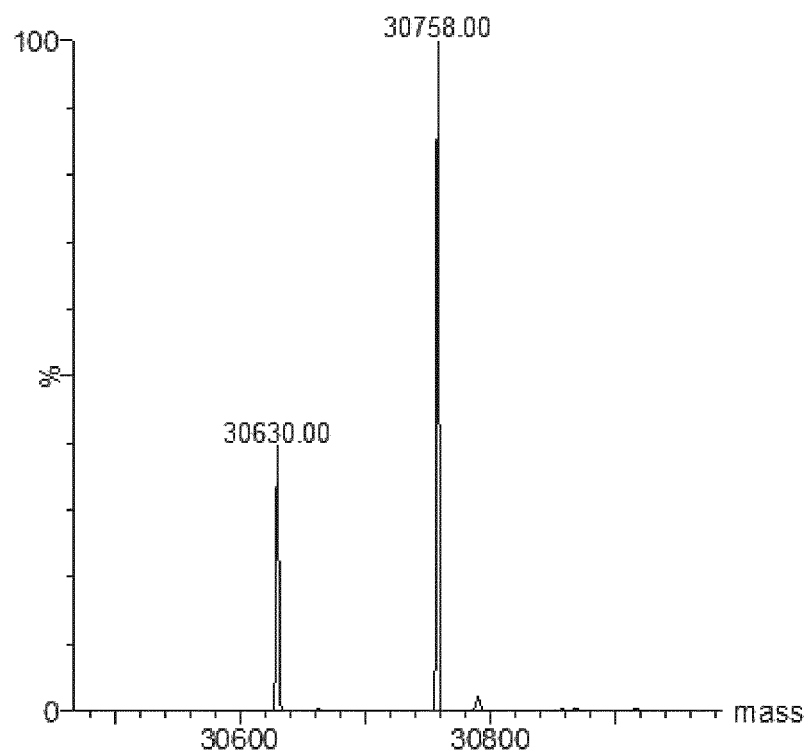
B
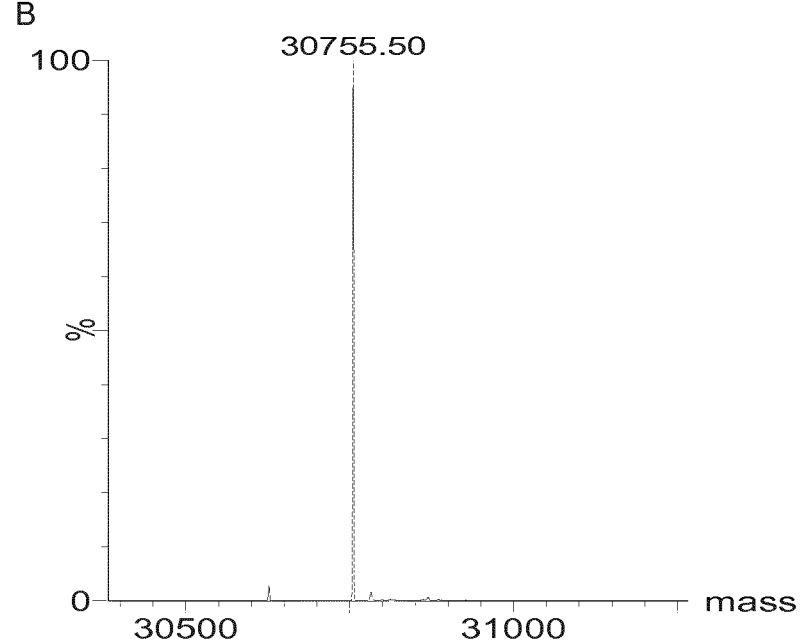

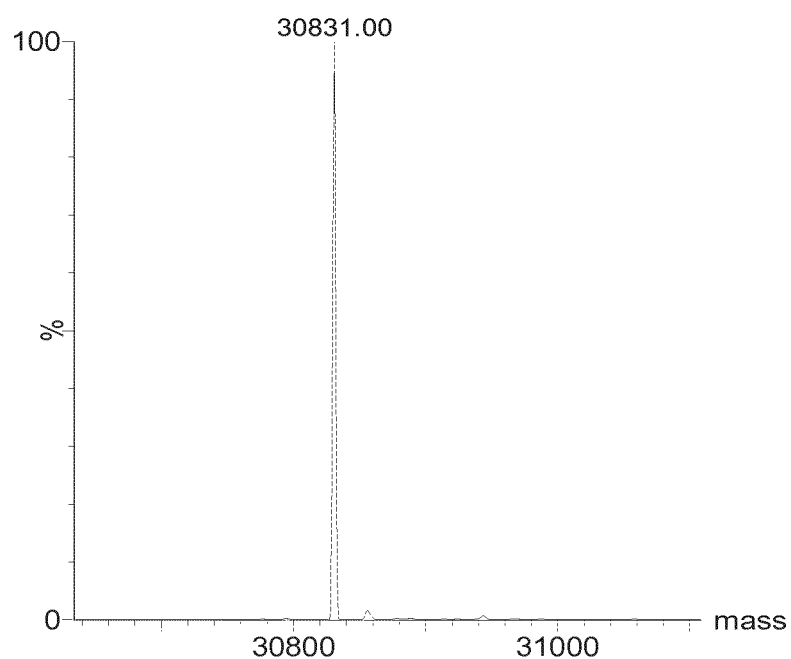

COILED-COIL CONNECTOR

CROSS-REFERENCE TO RELATED APPLICATIONS

This application is the U.S. national stage of International Patent Application No. PCT/EP2016/070590, filed on Sep. 1, 2016 and entitled COILED-COIL CONNECTOR, which claims the benefit of priority under 35 U.S.C. § 119 from European Patent Application No. 15183330.8, filed Sep. 1, 2015. The disclosures of the foregoing applications are incorporated herein by reference in their entirety.

SEQUENCE LISTING

The entire content of a Sequence Listing titled "Sequence_ Listing.txt," created on Feb. 14, 2018 and having a size of 42 kilobytes, which has been submitted in electronic form in connection with the present application, is hereby incorporated by reference herein in its entirety.

FIELD OF THE INVENTION

The invention refers to a connector having a helical coiled coil-type structure comprising at least two matching peptidic alpha-helices which form a coiled coil, said connector being improved by a terminal amino acid addition.

BACKGROUND OF THE INVENTION

Coiled coils are consisting of structural motifs in proteins, in which 2-7 alpha-helices are coiled together like the strands of a rope; dimers and trimers are the most common types. Such structures can improve the stability and folded structure of complex proteinaceous molecules. Coiled coils have been used to connect components of multimeric proteins, or proteinaceous constructs (characterized by one or more polypeptide chains and optionally further non-polypeptide components), including e.g., composite vaccine immungens or antibody fusion constructs.

Coiled coil helices have been used to stabilize Fv antibody fragments resulting in heterodimeric coiled-coil domains (Arndt et al. 2001. Helix-stabilized Fv (hsFv) antibody fragments: substituting the constant domains of a Fab fragment for a heterodimeric coiled-coil domain. *J Mol. Biol.* 312:221-228).

The coiled coil principle is also used for purification purposes (e.g., Chao et al 1998. Use of a heterodimeric coiled-coil system for biosensor application and affinity purification. J. Chromatogr. B Biomed. Sci. Appl. 715:307-329), as well as for tethering of protein to be tested as ligands for e.g. growth factors receptors (Boucher et al. 2009. Epidermal Growth Factor Tethered through Coiled-Coil Interactions Induces Cell Surface Receptor Phosphorylation. Bioconjug. Chem. 1569-1577).

WO2014009209A2 discloses a vaccine comprising a coiled coil formed by an immunogen and an adjuvant, wherein the adjuvant comprises at least an anti-CD32 moiety linked to a TLR9 ligand and a first peptidic alpha-helix, and the immunogen comprises at least one epitope and a second peptidic alpha-helix coiled to the first alpha-helix.

The first alpha-helix is typically made of (comprising or consisting of) a polyad repeat of a first motif. The matching second alpha-helix (comprising or consisting of a polyad repeat of a counter motif) self-assembles with the first one and thus forms a coiled coil, connecting the parts fused to each of the alpha-helices with high affinity.

US20150166610A1 and WO2015018806A1 describe an immunogenic composition stabilized by a C-terminal coiled coil domain.

WO2015006736A2 describes a fusion protein wherein an immunoglobulin is connected to a therapeutic agent by a coiled coil.

WO94/293332A1 describes polypeptides that are conformationally constricted in an intramolecular, antiparallel, coiled-coil stem loop arrangements. The loop segment comprises a connector between the carboxy terminus of a first alpha-helixal structure and the amino terminus of a second alpha-helical structure.

Richardson et al. (Science 1988, 240:1648-1652) describe amino acid preferences for specific locations at the ends of alpha helices. Results of a comparison of 215 alpha helices from 45 different globular protein structures showed a certain preference of specific amino acids at the C-cap or N-cap positions. Serrano et al. (Journal of Molecular Biology 1992, 227(2):544-559) describe the alpha-helix stability in proteins and the effect of mutations at the N-caps, C-caps and internal positions on stability.

WO2014187743A1 describes gastrin peptide immunogenic compositions comprising a coiled coil of two different alpha-helices.

The stability and folded structure of complex proteinaceous molecules is crucial when designing pharmaceutical agents such as immunogens.

SUMMARY OF THE INVENTION

It is the object of the invention to provide a coiled coil connector with improved stability and structure which can be used as a building block for designing composite polypeptids or proteins.

The object is solved by the subject matter as claimed.

According to the invention there is provided a connector of a helical coiled coil-type structure comprising a first and a second molecule, in particular wherein each of the first and second molecules is a proteinaceous molecule comprising a polypeptide moiety or a polypeptide chain, wherein the first molecule comprises a peptidic first alpha-helix and the second molecule comprises a peptidic second alpha-helix, which second alpha-helix is coiled to the first alpha-helix;

wherein the first alpha-helix comprises i) a C-terminal region consisting of a repeat of an amino acid motif a-$x_1$ and the C-terminal motif a-$x_1$-$x_2$; or ii) an N-terminal region consisting of a repeat of an amino acid motif $x_1$-a and the N-terminal motif $x_2$-$x_1$-a;

wherein a is a motif sequence of 4-8 amino acids;

$x_1$ is Lysine; and $x_2$ is an extension of the motif, wherein the extension consists of 1-10 amino acids, and wherein the extension does not comprise more than 4 consecutive amino acids incorporated in said motif a-$x_1$ or $x_1$-a.

Specifically, the amino acids of the extension are natural amino acids.

Specifically, the extension comprises at least one amino acid selected from the group consisting of Alanine, Glycine, Serine, Isoleucine, Leucine, Phenylalanine, Valine, and Proline.

Specifically, the extension comprises said selected amino acid within the first 1-4 amino acids extending the alpha-helix, in particular the terminus or cap of the (unextended) alpha-helix.

Specifically, the motif sequence a consists of a sequence of any of the natural amino acids. Preferably, the motif sequence comprises at least one hydrophobic amino acid to ensure a hydrophobic residue periodicity and alpha-helical propensity in a motif repeat.

Specifically, the connector comprises or consists of the coiled alpha-helices (i.e., the longitudinal assembly of the alpha-helices). The connector is specifically used as a building block to connect two molecules of the same structure (e.g., to obtain a homodimer), or two different molecules (e.g., to obtain a heterodimer). In particular, one or both of the molecules are proteinaceous, e.g., incorporating a polypeptide moiety which preferably consists of a polypeptide chain, particularly a polypeptide chain that is fused to the alpha-helix (used as connecting part) of the connector.

Specifically, each of said first and second alpha-helices comprises 2-9, preferably 3-5 repeats of matching amino acid motifs. The same number of repeats may be present on each of the alpha-helices, but also different number. For example, the number of coil repeats can be 3-5 in each of the peptidic alpha-helices, i.e., any of the combinations 3+3, 3+4, 3+5, 4+4, 4+5, 5+5, 4+3, 5+3 or 5+4.

Specifically, the repeat is a repeat of identical motifs or of motifs that differ from each other in at least one amino acid, typically 1 or 2 amino acids. Variants of a motif may be used, as long as such variant motifs are functional, i.e., wherein the alpha-helices are able to self-assemble with a high affinity, e.g., with a $K_D$ of less than $10^{-7}$ M or a $K_D$ of less than $10^{-8}$ M.

In case of a heterodimeric coiled coil, the typical number of coil repeats is specifically not more than 5, so to avoid undesired mismatches of the structure. In case of a heterodimeric coiled coil, it is typically desirable to employ a length of the peptide sequence with at least 3 repeats. Thereby the binding of the alpha-helices to each other is typically achieved with high affinity with a $K_D$ of less than $10^{-7}$ M or a $K_D$ of less than $10^{-8}$ M, preferably less than $10^{-9}$ M, or $10^{-10}$ M. However, although more repeats increase the affinity, this may be at the cost of increased homodimerisation.

Specifically, each of said first and second alpha-helices comprises repeats of an amino acid motif consisting of 6, 7, 8, or 9 amino acids, preferably 7 amino acids. Such motif is also named polyad because it consist of a number of consecutive amino acids, e.g., with a length of 6-9 amino acids. The 7 amino acid motif is typically used and herein referred to as a heptad. Alternatively, a hexad (i.e., 6 amino acids) motif, an octad (i.e., 8 amino acids) motif, or a nonad (i.e., 9 amino acids) motif may be used.

Specifically, the connector comprises a bundle of two to seven alpha-helices with matching amino acid repeat sequences in the helical coiled coil-type structure.

According to a specific embodiment, the first and second alpha-helices are coiled to a coiled-coil (in other words, assembled) double helix.

Two peptide strands with an alpha-helix structure which are coiled to each other, are herein referred to as a dimer. Specific examples include two alpha-helices or more, wherein the alpha-helices may be identical (homomer e.g., homodimer) or differ from each other (heteromer e.g., heterodimer). Trimers, tetramers or pentamers are, for instance, oligomers composed of three, four and five alpha-helices, respectively.

According to a specific aspect, the connector comprises or consists of a heterodimeric coiled-coil wherein the first alpha-helix is different from the second alpha-helix.

According to specific embodiments,
a) the motif $a-x_1$ is selected from the group consisting of SEQ ID 1, SEQ ID 3, SEQ ID 5, and SEQ ID 7; or b) the motif $x_1$-a is selected from the group consisting of SEQ ID 2, SEQ ID 4, SEQ ID 6, and SEQ ID 8.

Alternatively, any of the sequences described by Chao et al. (sic) or Litowsky et al. (2002. Designing heterodimeric two-stranded alpha-helical coiled-coils. Effects of hydrophobicity and alpha-helical propensity on protein folding, stability, and specificity. *J. Biol. Chem.* 277:37272-37279) or functional variants, which generate the specific coiled-coil type linkage, may be used:

According to specific examples,
a) the motif $a-x_1$ is SEQ ID 1 and the motif $a-x_1-x_2$ is any of SEQ ID 41, SEQ ID 69, or SEQ ID 71, which motif $a-x_1-x_2$ is optionally extended (e.g., at the carboxyl terminus) by one or more amino acids; or b) the motif $a-x_1$ is SEQ ID 3 and the motif $a-x_1-x_2$ is any of SEQ ID 43, SEQ ID 85, or SEQ ID 87, which motif $a-x_1-x_2$ is optionally extended (e.g., at the carboxyl terminus) by one or more amino acids; or c) the motif $a-x_1$ is SEQ ID 5 and the motif $a-x_1-x_2$ is any of SEQ ID 45, SEQ ID 101, or SEQ ID 103, which motif $a-x_1-x_2$ is optionally extended (e.g., at the carboxyl terminus) by one or more amino acids; or d) the motif $a-x_1$ is SEQ ID 7 and the motif $a-x_1-x_2$ is any of SEQ ID 47, SEQ ID 117, or SEQ ID 119, which motif $a-x_1-x_2$ is optionally extended (e.g., at the carboxyl terminus) by one or more amino acids; or e) the motif $x_1$-a is SEQ ID 2 and the motif $x_2-x_1$-a is any of SEQ ID 42, SEQ ID 77, or SEQ ID 79, which motif $x_2-x_1$-a is optionally extended (e.g., at the amino terminus) by one or more amino acids; or f) the motif $x_1$-a is SEQ ID 4 and the motif $x_2-x_1$-a is any of SEQ ID 44, SEQ ID 93, or SEQ ID 95, which motif $x_2-x_1$-a is optionally extended (e.g., at the amino terminus) by one or more amino acids; or g) the motif $x_1$-a is SEQ ID 6 and the motif $x_2-x_1$-a is any of SEQ ID 46, SEQ ID 109, or SEQ ID 111, which motif $x_2-x_1$-a is optionally extended (e.g., at the amino terminus) by one or more amino acids; or h) the motif $x_1$-a is SEQ ID 8 and the motif $x_2-x_1$-a is any of SEQ ID 48, SEQ ID 125, or SEQ ID 127, which motif $x_2-x_1$-a is optionally extended (e.g., at the amino terminus) by one or more amino acids.

Specifically,
a) the first alpha-helix comprises the motif $a-x_1$ and the second alpha-helix comprises the motif $x_1$-a; or b) the first alpha-helix comprises the motif $x_1$-a and the second alpha-helix comprises the motif $a-x_1$;

preferably wherein the alpha-helix comprising the motif $a-x_1$ further comprises the C-terminal motif $a-x_1-x_2$, and the alpha-helix comprising the motif $x_1$-a further comprises the N-terminal motif $x_2-x_1$-a.

A specific connector is provided, wherein
a)
i) the motif $a-x_1$ is SEQ ID 1;
ii) the motif $a-x_1-x_2$ is any of SEQ ID 41, SEQ ID 69, or SEQ ID 71;
iii) the motif $x_1$-a is SEQ ID 2; and
iv) the motif $x_2-x_1$-a is any of SEQ ID 42, SEQ ID 77, or SEQ ID 79;
or
b)
i) the motif $a-x_1$ is SEQ ID 3;
ii) the motif $a-x_1-x_2$ is any of SEQ ID 43, SEQ ID 85, or SEQ ID 87;
iii) the motif $x_1$-a is SEQ ID 4; and
iv) the motif $x_2-x_1$-a is any of SEQ ID 44, SEQ ID 93, or SEQ ID 95;

or c)
i) the motif a-x$_1$ is SEQ ID 5;
ii) the motif a-x$_1$-x$_2$ is any of SEQ ID 45, SEQ ID 101, or SEQ ID 103;
iii) the motif x$_1$-a is SEQ ID 6; and
iv) the motif x$_2$-x$_1$-a is any of SEQ ID 46, SEQ ID 109, or SEQ ID 111;

or d)
i) the motif a-x$_1$ is SEQ ID 7;
ii) the motif a-x$_1$-x$_2$ is any of SEQ ID 47, SEQ ID 117, or SEQ ID 119;
iii) the motif x$_1$-a is SEQ ID 8; and
iv) the motif x$_2$-x$_1$-a is any of SEQ ID 48, SEQ ID 125, or SEQ ID 127.

Specifically, the first or second alpha-helix comprises or consists of any of
i) any of SEQ ID 10, SEQ ID 68, or SEQ ID 70;
ii) any of SEQ ID 12, SEQ ID 72, or SEQ ID 73;
iii) any of SEQ ID 53, SEQ ID 74, or SEQ ID 75;
iv) any of SEQ ID 14, SEQ ID 76, or SEQ ID 78;
v) any of SEQ ID 16, SEQ ID 80, or SEQ ID 81;
vi) any of SEQ ID 55, SEQ ID 82, or SEQ ID 83;
vii) any of SEQ ID 18, SEQ ID 84, or SEQ ID 86;
viii) any of SEQ ID 20, SEQ ID 88, or SEQ ID 89;
ix) any of SEQ ID 57, SEQ ID 90, or SEQ ID 91;
x) any of SEQ ID 22, SEQ ID 92, or SEQ ID 94;
xi) any of SEQ ID 24, SEQ ID 96, or SEQ ID 97;
xii) any of SEQ ID 59, SEQ ID 98, or SEQ ID 99;
xiii) any of SEQ ID 26, SEQ ID 100, or SEQ ID 102;
xiv) any of SEQ ID 28, SEQ ID 104, or SEQ ID 105;
xv) any of SEQ ID 61, SEQ ID 106, or SEQ ID 107;
xvi) any of SEQ ID 30, SEQ ID 108, or SEQ ID 110;
xvii) any of SEQ ID 32, SEQ ID 112, or SEQ ID 113;
xviii) any of SEQ ID 63, SEQ ID 114, or SEQ ID 115;
xix) any of SEQ ID 34, SEQ ID 116, or SEQ ID 118;
xx) any of SEQ ID 36, SEQ ID 120, or SEQ ID 121;
xxi) any of SEQ ID 65, SEQ ID 122, or SEQ ID 123;
xxii) any of SEQ ID 38, SEQ ID 124, or SEQ ID 126;
xxiii) any of SEQ ID 40, SEQ ID 128, or SEQ ID 129; or
xxiv) any of SEQ ID 67, SEQ ID 130, or SEQ ID 131.

A specific embodiment is characterized by any of the following:
i) the first alpha-helix comprises or consists of any of SEQ ID 10, SEQ ID 68, or SEQ ID 70; and the second alpha-helix comprises or consists of SEQ ID 9;
ii) the first alpha-helix comprises or consists of any of SEQ ID 12, SEQ ID 72, or SEQ ID 73, and the second alpha-helix comprises or consists of SEQ ID 11;
iii) the first alpha-helix comprises or consists of any of SEQ ID 53, SEQ ID 74, or SEQ ID 75, and the second alpha-helix comprises or consists of SEQ ID 52;
iv) the first alpha-helix comprises or consists of any of SEQ ID 14, SEQ ID 76, or SEQ ID 78, and the second alpha-helix comprises or consists of SEQ ID 13;
v) the first alpha-helix comprises or consists of any of SEQ ID 16, SEQ ID 80, or SEQ ID 81, and the second alpha-helix comprises or consists of SEQ ID 15;
vi) the first alpha-helix comprises or consists of any of SEQ ID 55, SEQ ID 82, or SEQ ID 83, and the second alpha-helix comprises or consists of SEQ ID 54;
vii) the first alpha-helix comprises or consists of any of SEQ ID 18, SEQ ID 84, or SEQ ID 86, and the second alpha-helix comprises or consists of SEQ ID 17;
viii) the first alpha-helix comprises or consists of any of SEQ ID 20, SEQ ID 88, or SEQ ID 89, and the second alpha-helix comprises or consists of SEQ ID 19;
ix) the first alpha-helix comprises or consists of any of SEQ ID 57, SEQ ID 90, or SEQ ID 91, and the second alpha-helix comprises or consists of SEQ ID 56;
x) the first alpha-helix comprises or consists of any of SEQ ID 22, SEQ ID 92, or SEQ ID 94, and the second alpha-helix comprises or consists of SEQ ID 21;
xi) the first alpha-helix comprises or consists of any of SEQ ID 24, SEQ ID 96, or SEQ ID 97, and the second alpha-helix comprises or consists of SEQ ID 23;
xii) the first alpha-helix comprises or consists of any of SEQ ID 59, SEQ ID 98, or SEQ ID 99, and the second alpha-helix comprises or consists of SEQ ID 58;
xiii) the first alpha-helix comprises or consists of any of SEQ ID 26, SEQ ID 100, or SEQ ID 102, and the second alpha-helix comprises or consists of SEQ ID 25;
xiv) the first alpha-helix comprises or consists of any of SEQ ID 28, SEQ ID 104, or SEQ ID 105, and the second alpha-helix comprises or consists of SEQ ID 27;
xv) the first alpha-helix comprises or consists of any of SEQ ID 61, SEQ ID 106, or SEQ ID 107, and the second alpha-helix comprises or consists of SEQ ID 60;
xvi) the first alpha-helix comprises or consists of any of SEQ ID 30, SEQ ID 108, or SEQ ID 110, and the second alpha-helix comprises or consists of SEQ ID 29;
xvii) the first alpha-helix comprises or consists of any of SEQ ID 32, SEQ ID 112, or SEQ ID 113, and the second alpha-helix comprises or consists of SEQ ID 31;
xviii) the first alpha-helix comprises or consists of any of SEQ ID 63, SEQ ID 114, or SEQ ID 115, and the second alpha-helix comprises or consists of SEQ ID 62;
xix) the first alpha-helix comprises or consists of any of SEQ ID 34, SEQ ID 116, or SEQ ID 118, and the second alpha-helix comprises or consists of SEQ ID 33;
xx) the first alpha-helix comprises or consists of any of SEQ ID 36, SEQ ID 120, or SEQ ID 121, and the second alpha-helix comprises or consists of SEQ ID 35;
xxi) the first alpha-helix comprises or consists of any of SEQ ID 65, SEQ ID 122, or SEQ ID 123, and the second alpha-helix comprises or consists of SEQ ID 64;
xxii) the first alpha-helix comprises or consists of any of SEQ ID 38, SEQ ID 124, or SEQ ID 126, and the second alpha-helix comprises or consists of SEQ ID 37;
xxiii) the first alpha-helix comprises or consists of any of SEQ ID 40, SEQ ID 128, or SEQ ID 129, and the second alpha-helix comprises or consists of SEQ ID 39; or
xxiv) the first alpha-helix comprises or consists of any of SEQ ID 67, SEQ ID 130, or SEQ ID 131, and the second alpha-helix comprises or consists of SEQ ID 66.

The various motifs are further described in Table 1.

TABLE 1

Motif type, sequences and exemplary repeats

| Motif sequence | Type | exemplary terminal region: 3 or 4 repeats |
|---|---|---|
| EIAALEK<br>SEQ ID 1 | a-x$_1$ | E3:<br>EIAALEKEIAALEKEIAALEK (SEQ ID 9) |

TABLE 1-continued

Motif type, sequences and exemplary repeats

Motif sequence Type exemplary terminal region: 3 or 4 repeats

| Motif sequence | Type | exemplary terminal region: 3 or 4 repeats |
|---|---|---|
| EIAALEK SEQ ID 1 | a-$x_1$ | E3 extended at the C-terminus:<br>EIAALEKEIAALEKEIAALEKA (SEQ ID 10)<br>C-terminal motif a-$x_1$-$x_2$: EIAALEKA (SEQ ID 41)<br>EIAALEKEIAALEKEIAALEKG (SEQ ID 68)<br>C-terminal motif a-$x_1$-$x_2$: EIAALEKG (SEQ ID 69)<br>EIAALEKEIAALEKEIAALEKS (SEQ ID 70)<br>C-terminal motif a-$x_1$-$x_2$: EIAALEKS (SEQ ID 71) |
| EIAALEK SEQ ID 1 | a-$x_1$ | E4:<br>EIAALEKEIAALEKEIAALEKEIAALEK (SEQ ID 11) |
| EIAALEK SEQ ID 1 | a-$x_1$ | E4 extended at the C-terminus:<br>EIAALEKEIAALEKEIAALEKEIAALEKA (SEQ ID 12)<br>C-terminal motif a-$x_1$-$x_2$: EIAALEKA (SEQ ID 41)<br>EIAALEKEIAALEKEIAALEKEIAALEKG (SEQ ID 72)<br>C-terminal motif a-$x_1$-$x_2$: EIAALEKG (SEQ ID 69)<br>EIAALEKEIAALEKEIAALEKEIAALEKS (SEQ ID 73)<br>C-terminal motif a-$x_1$-$x_2$: EIAALEKS (SEQ ID 71) |
| EIAALEK SEQ ID 1 | a-$x_1$ | E5:<br>EIAALEKEIAALEKEIAALEKEIAALEKEIAALEK (SEQ ID 52) |
| EIAALEK SEQ ID 1 | a-$x_1$ | E5 extended at the C-terminus:<br>EIAALEKEIAALEKEIAALEKEIAALEKEIAALEKA (SEQ ID 53)<br>C-terminal motif a-$x_1$-$x_2$: EIAALEKA (SEQ ID 41)<br>EIAALEKEIAALEKEIAALEKEIAALEKEIAALEKG (SEQ ID 74)<br>C-terminal motif a-$x_1$-$x_2$: EIAALEKG (SEQ ID 69)<br>EIAALEKEIAALEKEIAALEKEIAALEKEIAALEKS (SEQ ID 75)<br>C-terminal motif a-$x_1$-$x_2$: EIAALEKS (SEQ ID 71) |
| KIAALKE SEQ ID 2 | $x_1$-a | K3:<br>KIAALKEKIAALKEKIAALKE (SEQ ID 13) |
| KIAALKE SEQ ID 2 | $x_1$-a | K3 extended at the N-terminus:<br>AKIAALKEKIAALKEKIAALKE (SEQ ID 14)<br>N-terminal motif $x_2$-$x_1$-a: AKIAALKE (SEQ ID 42)<br>GKIAALKEKIAALKEKIAALKE (SEQ ID 76)<br>N-terminal motif $x_2$-$x_1$-a: GKIAALKE (SEQ ID 77)<br>SKIAALKEKIAALKEKIAALKE (SEQ ID 78)<br>N-terminal motif $x_2$-$x_1$-a: SKIAALKE (SEQ ID 79) |
| KIAALKE SEQ 1D2 | $x_1$-a | K4:<br>KIAALKEKIAALKEKIAALKEKIAALKE (SEQ ID 15) |
| KIAALKE SEQ ID 2 | $x_1$-a | K4 extended at the N-terminus:<br>AKIAALKEKIAALKEKIAALKEKIAALKE (SEQ ID 16)<br>N-terminal motif $x_2$-$x_1$-a: AKIAALKE (SEQ ID 42)<br>GKIAALKEKIAALKEKIAALKEKIAALKE (SEQ ID 80)<br>N-terminal motif $x_2$-$x_1$-a: GKIAALKE (SEQ ID 77)<br>SKIAALKEKIAALKEKIAALKEKIAALKE (SEQ ID 81)<br>N-terminal motif $x_2$-$x_1$-a: SKIAALKE (SEQ ID 79) |
| KIAALKE SEQ ID 2 | $x_1$-a | K5:<br>KIAALKEKIAALKEKIAALKEKIAALKEKIAALKE (SEQ ID 54) |
| KIAALKE SEQ ID 2 | $x_1$-a | K5 extended at the N-terminus:<br>AKIAALKEKIAALKEKIAALKEKIAALKEKIAALKE (SEQ ID 55)<br>N-terminal motif $x_2$-$x_1$-a: AKIAALKE (SEQ ID 42)<br>GKIAALKEKIAALKEKIAALKEKIAALKEKIAALKE (SEQ ID 82)<br>N-terminal motif $x_2$-$x_1$-a: GKIAALKE (SEQ ID 77)<br>SKIAALKEKIAALKEKIAALKEKIAALKEKIAALKE (SEQ ID 83)<br>N-terminal motif $x_2$-$x_1$-a: SKIAALKE (SEQ ID 79) |
| EISALEK SEQ ID 3 | a-$x_1$ | E3:<br>EISALEKEISALEKEISALEK (SEQ ID 17) |
| EISALEK SEQ ID 3 | a-$x_1$ | E3 extended at the C-terminus:<br>EISALEKEISALEKEISALEKA (SEQ ID 18)<br>C-terminal motif a-$x_1$-$x_2$: EISALEKA (SEQ ID 43)<br>EISALEKEISALEKEISALEKG (SEQ ID 84)<br>C-terminal motif a-$x_1$-$x_2$: EISALEKG (SEQ ID 85)<br>EISALEKEISALEKEISALEKS (SEQ ID 86)<br>C-terminal motif a-$x_1$-$x_2$: EISALEKS (SEQ ID 87) |

TABLE 1-continued

Motif type, sequences and exemplary repeats

Motif sequence  Type     exemplary terminal region: 3 or 4 repeats

EISALEK         a-$x_1$  E4:
SEQ ID 3                 EISALEKEISALEKEISALEKEISALEK (SEQ ID 19)

EISALEK         a-$x_1$  E4 extended at the C-terminus:
SEQ ID 3                 EISALEKEISALEKEISALEKEISALEKA (SEQ ID 20)
                         C-terminal motif a-$x_1$-$x_2$: EISALEKA (SEQ ID 43)
                         EISALEKEISALEKEISALEKEISALEKG (SEQ ID 88)
                         C-terminal motif a-$x_1$-$x_2$: EISALEKG (SEQ ID 85)
                         EISALEKEISALEKEISALEKEISALEKS (SEQ ID 89)
                         C-terminal motif a-$x_1$-$x_2$: EISALEKS (SEQ ID 87)

EISALEK         a-$x_1$  E5:
SEQ ID 3                 EISALEKEISALEKEISALEKEISALEKEISALEK (SEQ ID 56)

EISALEK         a-$x_1$  E5 extended at the C-terminus:
SEQ ID 3                 EISALEKEISALEKEISALEKEISALEKEISALEKA (SEQ ID 57)
                         C-terminal motif a-$x_1$-$x_2$: EISALEKA (SEQ ID 43)
                         EISALEKEISALEKEISALEKEISALEKEISALEKG (SEQ ID 90)
                         C-terminal motif a-$x_1$-$x_2$: EISALEKG (SEQ ID 85)
                         EISALEKEISALEKEISALEKEISALEKEISALEKS (SEQ ID 91)
                         C-terminal motif a-$x_1$-$x_2$: EISALEKS (SEQ ID 87)

KISALKE         $x_1$-a  K3:
SEQ ID 4                 KISALKEKISALKEKISALKE (SEQ ID 21)

KISALKE         $x_1$-a  K3 extended at the N-terminus:
SEQ ID 4                 AKISALKEKISALKEKISALKE (SEQ ID 22)
                         N-terminal motif $x_2$-$x_1$-a: AKISALKE (SEQ ID 44)
                         GKISALKEKISALKEKISALKE (SEQ ID 92)
                         N-terminal motif $x_2$-$x_1$-a: GKISALKE (SEQ ID 93)
                         SKISALKEKISALKEKISALKE (SEQ ID 94)
                         N-terminal motif $x_2$-$x_1$-a: SKISALKE (SEQ ID 95)

KISALKE         $x_1$-a  K4:
SEQ ID 4                 KISALKEKISALKEKISALKEKISALKE (SEQ ID 23)

KISALKE         $x_1$-a  K4 extended at the N-terminus:
SEQ ID 4                 AKISALKEKISALKEKISALKEKISALKE (SEQ ID 24)
                         N-terminal motif $x_2$-$x_1$-a: AKISALKE (SEQ ID 44)
                         GKISALKEKISALKEKISALKEKISALKE (SEQ ID 96)
                         N-terminal motif $x_2$-$x_1$-a: GKISALKE (SEQ ID 93)
                         SKISALKEKISALKEKISALKEKISALKE (SEQ ID 97)
                         N-terminal motif $x_2$-$x_1$-a: SKISALKE (SEQ ID 95)

KISALKE         $x_1$-a  K5:
SEQ ID 4                 KISALKEKISALKEKISALKEKISALKEKISALKE (SEQ ID 58)

KISALKE         $x_1$-a  K5 extended at the N-terminus:
SEQ ID 4                 AKISALKEKISALKEKISALKEKISALKEKISALKE (SEQ ID 59)
                         N-terminal motif $x_2$-$x_1$-a: AKISALKE (SEQ ID 44)
                         GKISALKEKISALKEKISALKEKISALKEKISALKE (SEQ ID 98)
                         N-terminal motif $x_2$-$x_1$-a: GKISALKE (SEQ ID 93)
                         SKISALKEKISALKEKISALKEKISALKEKISALKE (SEQ ID 99)
                         N-terminal motif $x_2$-$x_1$-a: SKISALKE (SEQ ID 95)

EVAALEK         a-$x_1$  E3:
SEQ ID 5                 EVAALEKEVAALEKEVAALEK (SEQ ID 25)

EVAALEK         a-$x_1$  E3 extended at the C-terminus:
SEQ ID 5                 EVAALEKEVAALEKEVAALEKA (SEQ ID 26)
                         C-terminal motif a-$x_1$-$x_2$: EVAALEKA (SEQ ID 45)
                         EVAALEKEVAALEKEVAALEKG (SEQ ID 100)
                         C-terminal motif a-$x_1$-$x_2$: EVAALEKG (SEQ ID 101)
                         EVAALEKEVAALEKEVAALEKS (SEQ ID 102)
                         C-terminal motif a-$x_1$-$x_2$: EVAALEKS (SEQ ID 103)

EVAALEK         a-$x_1$  E4:
SEQ ID 5                 EVAALEKEVAALEKEVAALEKEVAALEK (SEQ ID 27)

EVAALEK         a-$x_1$  E4 extended at the C-terminus:
SEQ ID 5                 EVAALEKEVAALEKEVAALEKEVAALEKA (SEQ ID 28)
                         C-terminal motif a-$x_1$-$x_2$: EVAALEKA (SEQ ID 45)
                         EVAALEKEVAALEKEVAALEKEVAALEKG (SEQ ID 104)

TABLE 1-continued

Motif type, sequences and exemplary repeats

| Motif sequence | Type | exemplary terminal region: 3 or 4 repeats |
|---|---|---|
| | | C-terminal motif $a$-$x_1$-$x_2$: EVAALEKG (SEQ ID 101)<br>EVAALEKEVAALEKEVAALEKEVAALEKS (SEQ ID 105)<br>C-terminal motif $a$-$x_1$-$x_2$: EVAALEKS (SEQ ID 103) |
| EVAALEK<br>SEQ ID 5 | $a$-$x_1$ | E5:<br>EVAALEKEVAALEKEVAALEKEVAALEKEVAALEK (SEQ ID 60) |
| EVAALEK<br>SEQ ID 5 | $a$-$x_1$ | E5 extended at the C-terminus:<br>EVAALEKEVAALEKEVAALEKEVAALEKEVAALEKA (SEQ ID 61)<br>C-terminal motif $a$-$x_1$-$x_2$: EVAALEKA (SEQ ID 45)<br>EVAALEKEVAALEKEVAALEKEVAALEKEVAALEKG (SEQ ID 106)<br>C-terminal motif $a$-$x_1$-$x_2$: EVAALEKG (SEQ ID 101)<br>EVAALEKEVAALEKEVAALEKEVAALEKEVAALEKS (SEQ ID 107)<br>C-terminal motif $a$-$x_1$-$x_2$: EVAALEKS (SEQ ID 103) |
| KVAALKE<br>SEQ ID 6 | $x_1$-$a$ | K3:<br>KVAALKEKVAALKEKVAALKE (SEQ ID 29) |
| KVAALKE<br>SEQ ID 6 | $x_1$-$a$ | K3 extended at the N-terminus:<br>AKVAALKEKVAALKEKVAALKE (SEQ ID 30)<br>N-terminal motif $x_2$-$x_1$-$a$: AKVAALKE (SEQ ID 46)<br>GKVAALKEKVAALKEKVAALKE (SEQ ID 108)<br>N-terminal motif $x_2$-$x_1$-$a$: GKVAALKE (SEQ ID 109)<br>SKVAALKEKVAALKEKVAALKE (SEQ ID 110)<br>N-terminal motif $x_2$-$x_1$-$a$: SKVAALKE (SEQ ID 111) |
| KVAALKE<br>SEQ ID 6 | $x_1$-$a$ | K4:<br>KVAALKEKVAALKEKVAALKEKVAALKE (SEQ ID 31) |
| KVAALKE<br>SEQ ID 6 | $x_1$-$a$ | K4 extended at the N-terminus:<br>AKVAALKEKVAALKEKVAALKEKVAALKE (SEQ ID 32)<br>N-terminal motif $x_2$-$x_1$-$a$: AKVAALKE (SEQ ID 46)<br>GKVAALKEKVAALKEKVAALKEKVAALKE (SEQ ID 112)<br>N-terminal motif $x_2$-$x_1$-$a$: GKVAALKE (SEQ ID 109)<br>SKVAALKEKVAALKEKVAALKEKVAALKE (SEQ ID 113)<br>N-terminal motif $x_2$-$x_1$-$a$: SKVAALKE (SEQ ID 111) |
| KVAALKE<br>SEQ ID 6 | $x_1$-$a$ | K5:<br>KVAALKEKVAALKEKVAALKEKVAALKEKVAALKE (SEQ ID 62) |
| KVAALKE<br>SEQ ID 6 | $x_1$-$a$ | K5 extended at the N-terminus:<br>AKVAALKEKVAALKEKVAALKEKVAALKEKVAALKE (SEQ ID 63)<br>N-terminal motif $x_2$-$x_1$-$a$: AKVAALKE (SEQ ID 46)<br>GKVAALKEKVAALKEKVAALKEKVAALKEKVAALKE (SEQ ID 114)<br>N-terminal motif $x_2$-$x_1$-$a$: GKVAALKE (SEQ ID 109)<br>SKVAALKEKVAALKEKVAALKEKVAALKEKVAALKE (SEQ ID 115)<br>N-terminal motif $x_2$-$x_1$-$a$: SKVAALKE (SEQ ID 111) |
| EVSALEK<br>SEQ ID 7 | $a$-$x_1$ | E3:<br>EVSALEKEVSALEKEVSALEK (SEQ ID 33) |
| EVSALEK<br>SEQ ID 7 | $a$-$x_1$ | E3 extended at the C-terminus:<br>EVSALEKEVSALEKEVSALEKA (SEQ ID 34)<br>C-terminal motif: EVSALEKA (SEQ ID 47)<br>EVSALEKEVSALEKEVSALEKG (SEQ ID 116)<br>C-terminal motif: EVSALEKG (SEQ ID 117)<br>EVSALEKEVSALEKEVSALEKS (SEQ ID 118)<br>C-terminal motif: EVSALEKS (SEQ ID 119) |
| EVSALEK<br>SEQ ID 7 | $a$-$x_1$ | E4:<br>EVSALEKEVSALEKEVSALEKEVSALEK (SEQ ID 35) |
| EVSALEK<br>SEQ ID 7 | $a$-$x_1$ | E4 extended at the C-terminus:<br>EVSALEKEVSALEKEVSALEKEVSALEKA (SEQ ID 36)<br>C-terminal motif: EVSALEKA (SEQ ID 47)<br>EVSALEKEVSALEKEVSALEKEVSALEKG (SEQ ID 120)<br>C-terminal motif: EVSALEKG (SEQ ID 117)<br>EVSALEKEVSALEKEVSALEKEVSALEKS (SEQ ID 121)<br>C-terminal motif: EVSALEKS (SEQ ID 119) |
| EVSALEK<br>SEQ ID 7 | $a$-$x_1$ | E5:<br>EVSALEKEVSALEKEVSALEKEVSALEKEVSALEK (SEQ ID 64) |
| EVSALEK<br>SEQ ID 7 | $a$-$x_1$ | E5 extended at the C-terminus:<br>EVSALEKEVSALEKEVSALEKEVSALEKEVSALEKA (SEQ ID 65)<br>C-terminal motif: EVSALEKA (SEQ ID 47) |

TABLE 1-continued

Motif type, sequences and exemplary repeats

| Motif sequence | Type | exemplary terminal region: 3 or 4 repeats |
|---|---|---|
| | | EVSALEKEVSALEKEVSALEKEVSALEKEVSALEKG (SEQ ID 122)<br>C-terminal motif: EVSALEKG (SEQ ID 117)<br>EVSALEKEVSALEKEVSALEKEVSALEKEVSALEKS (SEQ ID 123)<br>C-terminal motif: EVSALEKS (SEQ ID 119) |
| KVSALKE<br>SEQ ID 8 | $x_1$-a | K3:<br>KVSALKEKVSALKEKVSALKE (SEQ ID 37) |
| KVSALKE<br>SEQ ID 8 | $x_1$-a | K3 extended at the N-terminus:<br>AKVSALKEKVSALKEKVSALKE (SEQ ID 38)<br>N-terminal motif $x_2$-$x_1$-a: AKVSALKE (SEQ ID 48)<br>GKVSALKEKVSALKEKVSALKE (SEQ ID 124)<br>N-terminal motif $x_2$-$x_1$-a: GKVSALKE (SEQ ID 125)<br>SKVSALKEKVSALKEKVSALKE (SEQ ID 126)<br>N-terminal motif $x_2$-$x_1$-a: SKVSALKE (SEQ ID 127) |
| KVSALKE<br>SEQ ID 8 | $x_1$-a | K4:<br>KVSALKEKVSALKEKVSALKEKVSALKE (SEQ ID 39) |
| KVSALKE<br>SEQ ID 8 | $x_1$-a | K4 extended at the N-terminus:<br>AKVSALKEKVSALKEKVSALKEKVSALKE (SEQ ID 40)<br>N-terminal motif $x_2$-$x_1$-a: AKVSALKE (SEQ ID 48)<br>GKVSALKEKVSALKEKVSALKEKVSALKE (SEQ ID 128)<br>N-terminal motif $x_2$-$x_1$-a: GKVSALKE (SEQ ID 125)<br>SKVSALKEKVSALKEKVSALKEKVSALKE (SEQ ID 129)<br>N-terminal motif $x_2$-$x_1$-a: SKVSALKE (SEQ ID 127) |
| KVSALKE<br>SEQ ID 8 | $x_1$-a | K5:<br>KVSALKEKVSALKEKVSALKEKVSALKEKVSALKE (SEQ ID 66) |
| KVSALKE<br>SEQ ID 8 | $x_1$-a | K5 extended at the N-terminus:<br>AKVSALKEKVSALKEKVSALKEKVSALKEKVSALKE (SEQ ID 67)<br>N-terminal motif $x_2$-$x_1$-a: AKVSALKE (SEQ ID 48)<br>GKVSALKEKVSALKEKVSALKEKVSALKEKVSALKE (SEQ ID 130)<br>N-terminal motif $x_2$-$x_1$-a: GKVSALKE (SEQ ID 125)<br>SKVSALKEKVSALKEKVSALKEKVSALKEKVSALKE (SEQ ID 131)<br>N-terminal motif $x_2$-$x_1$-a: SKVSALKE (SEQ ID 127) |

According to specific embodiments, the first and second alpha-helices are either parallel or anti-parallel alpha-helices.

According to specific examples, in a parallel assembly, the C-terminal region of the first alpha-helix is assembled to the C-terminal region of the second alpha-helix; or the N-terminal region of the first alpha-helix is assembled to the N-terminal region of the second alpha-helix. When the connecting strands are fused to an amino acid sequence, both strands can comprise the alpha-helix as a C-terminal domain, or both strands can comprise the alpha-helix as a N-terminal domain.

Alternatively, in a parallel assembly, the C-terminal or N-terminal region of the first alpha-helix can be assembled to the second alpha-helix in the same directional (parallel) way, however, the second alpha-helix can be located within a polypeptide chain, i.e., not including a terminus, also understood as an inner domain, wherein the second alpha-helix is not fused to another polypeptide sequence at a terminus, but incorporated within an amino acid sequence, such that it comprises an N-terminal or C-terminal extension by any other polypeptide sequence or domain, which is preferably not characterized by an alpha-helical structure that could interfere with the coiled coil of the connector.

In an anti-parallel assembly, the C-terminal region of the first alpha-helix is assembled to the N-terminal region of the second alpha-helix, or vice versa. Alternatively, in an anti-parallel assembly, the C-terminal or N-terminal region of the first alpha-helix can be assembled to the second alpha-helix in the opposite directional (anti-parallel) way, however, the second alpha-helix can be located within a polypeptide chain, i.e., not including a terminus, also understood as an inner domain, wherein the second alpha-helix is not fused to another polypeptide sequence at a terminus, but incorporated within an amino acid sequence, such that it comprises an N-terminal or C-terminal extension by any other polypeptide sequence or domain, which is preferably not characterized by an alpha-helical structure that could interfere with the coiled coil of the connector.

According to a specific embodiment, $x_2$ consists of 1-5 consecutive amino acids (herein also referred to as "extension"), preferably 1-4, or 1-3, or 1-2 amino acids, wherein the extension comprises at least one of the preferred extending amino acids which is selected from the group consisting of Alanine, Glycine, Serine, Isoleucine, Leucine, Phenylalanine, Valine, and Proline, and optional further amino acids (of any type, e.g., any of the 20 natural amino acids may be used). Specifically, $x_2$ consists of only 1 amino acid which extends the coil sequence, either at the N-terminus (N-terminal extension), or at the C-terminus (C-terminal extension). Preferably, any of Alanine, Glycine or Serine is used for the extension. Specifically, $x_2$ consists of any of Alanine, Glycine or Serine only, or any of Alanine, Glycine or Serine, which is optionally extended by 1, 2, 3, or 4 further consecutive amino acids (of any type, e.g., any of the 20 natural amino acids may be used), so that the amino acid following the terminal region of an alpha-helix is any of Alanine, Glycine or Serine, and the terminus of the alpha-helix may be any of Alanine, Glycine or Serine, or any other amino acid.

Specifically, the extension does not comprise more than 4 consecutive amino acids incorporated in the motif a-$x_1$ or $x_1$-a, as the case may be. This is to avoid unspecific interaction or interference of the coil motif(s) with the extension.

According to a specific embodiment, a) the extension does not comprise Lysine, and/or b) the amino acid following the terminal region of an alpha-helix is not Lysine, and/or c) the C-terminal amino acid is not Lysine.

According to a preferred embodiment, said first and second alpha-helices are specifically binding to each other with a $K_D$ of less than $10^{-7}$M, preferably less than $10^{-8}$ M, or less than $10^{-9}$ M, or less than $10^{-10}$ M, or less than $10^{-11}$ M, or even with a $K_D$ in the picomolar range.

The invention further provides a multimeric or composite protein comprising at least two polypeptide chains connected to each other by a connector as described herein, wherein a first polypeptide chain incorporates the first alpha-helix, and the second first polypeptide chain incorporates the second alpha-helix; and wherein the first and second polypeptide chains are connected by the helical coiled-coil type structure of the first and second alpha-helices.

Specifically, a) the first polypeptide chain incorporating the first alpha-helix comprises the C-terminal region consisting of a repeat of an amino acid motif a-$x_1$ and the C-terminal motif a-$x_1$-$x_2$; and the second polypeptide chain incorporates the second alpha-helix as a parallel alpha-helix within a non-terminal region or in the C-terminal region; or b) the first polypeptide chain incorporating the first alpha-helix comprises the C-terminal region consisting of a repeat of an amino acid motif a-$x_1$ and the C-terminal motif a-$x_1$-$x_2$; and the second polypeptide chain incorporates the second alpha-helix as an anti-parallel alpha-helix within a non-terminal region or in the N-terminal region, or c) the first polypeptide chain incorporating the first alpha-helix comprises the N-terminal region consisting of a repeat of an amino acid motif $x_1$-a and the N-terminal motif $x_2$-$x_1$-a; and the second polypeptide chain incorporates the second alpha-helix as a parallel alpha-helix within a non-terminal region or in the N-terminal region; or d) the first polypeptide chain incorporating the first alpha-helix comprises the C-terminal region consisting of a repeat of an amino acid motif $x_1$-a and the N-terminal motif $x_2$-$x_1$-a; and the second polypeptide chain incorporates the second alpha-helix as an anti-parallel alpha-helix within a non-terminal region or in the C-terminal region.

Specifically, two or more polypeptide chains may be assembled by the connector as described herein, wherein at least two polypeptide chains (or each of the polypeptide chains) comprise a domain which is characterized by the alpha-helical structure.

According to a specific aspect, the protein is selected from the group consisting of a) a vaccine component comprising a vaccine antigen and an adjuvant;

b) an antibody or antibody format wherein each of the two polypeptide chains incorporates at least one antibody domain;

c) an antibody derivative comprising an antibody and a non-antibody component, wherein at least one polypeptide chain of the antibody is connected to another polypeptide chain incorporating the component, preferably wherein the component is any of an organic and inorganic molecule, in particular a label, tag, enzyme, receptor, ligand, toxin, lipid, carbohydrate, or nucleic acid; and d) an affinity material, wherein a receptor or ligand is connected to a carrier e.g., a solid phase for purification of receptor specific ligands or for testing affinities of different variants of ligand.

The invention further provides for a method of producing a protein as described herein, comprising a) providing a first host cell incorporating a first heterologous nucleic acid encoding the first polypeptide chain;

b) providing a second host cell incorporating a second heterologous nucleic acid encoding the second polypeptide chain;

c) cultivating said host cells under conditions to express said first and second polypeptide chains in the cell culture; and d) connecting said first and second polypeptide chains through the helical coiled coil-type structure;

preferably wherein the first and/or second host cell is a mammalian or yeast host cell.

Such connection is preferably by self-assembly of the polypeptide chains, either in the cell culture, or upon isolation and optional purification of the polypeptide chains.

According to a specific aspect, the method comprises the steps:

a) providing a host cell incorporating
  (i) a first heterologous nucleic acid encoding the first polypeptide chain; and
  (ii) a second heterologous nucleic acid encoding the second polypeptide chain;

b) cultivating said host cell under conditions to express said first and second polypeptide chains in the cell culture; and c) connecting said first and second polypeptide chains through the helical coiled coil-type structure, preferably wherein the host cell is a mammalian or yeast host cell.

Specifically, the host cell incorporating the first nucleic acid and optionally further incorporating the second nucleic acid is a mammalian or yeast host cell. Such host cells would have an increased risk of cleaving any C-terminal Lysine. By the extension as described herein, the terminal Lysine would be masked, and surprisingly the affinity of connection between the coiled coils, could be even improved.

The invention further provides for a preparation of a protein obtainable by the method as described herein, wherein at least 90% of the protein molecules comprise the correct C-terminal and N-terminal regions of the polypeptide chains encoded by the first and second nucleic acids. Specifically, when employing a host cells which is any of a mammalian or yeast host cell, the alpha-helix comprising Lysine as an N-terminal or C-terminal amino acid, would be in a large number of molecules (e.g. in up to 40% of all molecules) cleaved from the terminus. By the extension of the alpha-helix by at least one amino acid as described herein, the percentage of the molecules characterized by the correct amino acid terminus i.e., the terminus which is encoded by the respective nucleic acid sequence, can be significantly increased, e.g. to 90% or more, e.g. at least 95%, or even at least 99%, as determined by mass spectrometry.

Specifically preferred host cells for expressing at least the first polypeptide chain are mammalian host cells, which are of human, hamster, or murine origin. Specifically, any of HEK293, CHO, BHK, HeLa, MDCK, NIH3T3, NS0, PER.C6, SP2/0 and VERO cells may be used.

Alternatively, specifically preferred host cells for expressing at least the first polypeptide chain are yeast host cells, which are of *Pichia, Saccharomyces, Candida, Torulopsis,* Arxula, Hensenula, *Yarrowia, Kluyveromyces,* or *Komagataella* origin, preferably a methylotrophic yeast. Specifically, any of *P. pastoris, Komagataella pastoris, K. phaffii,* or *K. pseudopastoris*, or *S. cerevisiae* may be used.

The invention further provides a kit of components for preparing the connector or the multimeric protein as described herein, e.g. a pharmaceutical kit comprising one or more containers filled with the components. Each of the alpha-helices or the polypeptide chains comprising a single (or only one) alpha-helix may be provided as separate parts, and together as a kit of parts to prepare the connector or the multimeric protein, e.g. freshly prepare such composite construct by mixing and assembly of the parts.

It is specifically understood that the connector or the multimeric protein as described herein are non-naturally occurring, e.g. provided as a composition comprising polypeptide chains or other components connected to each other by the coiled coil, which composition does not occur in nature.

FIGURES

FIG. 1: Sequence of an exemplary scFv-coil1 (SEQ ID 49)
Underlined: VH and VL domains fused by a flexible linking sequence; the VH and VL domain sequences are obtained from a monoclonal antibody IV.3 that specifically recognizes CD32a (Stuart et al. (1987) J. Exp. Med. 166: 1668).
Normal type set: flexible linker (maybe any linker);
In italics: pepE coil: 5 repeats of a heptad motif, C-terminal Lysine (italics and bold).

FIG. 2: Sequence of an exemplary scFv-coil1ala (SEQ ID 50)
Underlined: VH and VL domains fused by a flexible linking sequence
Normal type set: flexible linker (maybe any linker);
In italics: pepE coil: 5 repeats of a heptad motif, C-terminal Alanine (italics and bold) as a C-terminal extension.

FIG. 3: pepK (SEQ ID 51)
In italics: pepK coil: 5 repeats of a heptad motif, N-terminal Lysine (italics and bold).

FIG. 4:
A: Mass spectrometry scFV-coil1 from HEK293 cells
The expected molecular weight (MW) based on the sequence of FIG. 1 is 30764 Da.
The MW found) are 30755.5 Da (~60% of total material) and 30630 Da (~40% of total material) which corresponds to expected MW minus Lys(289)
B: Mass spectrometry scFV-coil1 from S2 Insect cells
The expected molecular weight (MW) based on the sequence of FIG. 1 is 30764 Da.
The MW found is 30755.5 Da indicating full length protein.
C: Mass spectrometry scFV-coil1ala from HEK293 cells
The expected molecular weight (MW) based on the sequence of FIG. 2 is 30835.4 Da.
The MW found is 30831.0 Da indicating full length protein FIG. 5: Affinity analyses of pepK and scFV-coil1 or ScFV-coil1ala.

DETAILED DESCRIPTION OF THE INVENTION

Specific terms as used throughout the specification have the following meaning.

The term "coil" as used herein shall mean a motif consisting of an amino acid sequence and a three-dimensional structure which is at least part of a peptidic alpha-helix. The coil repeat can make up a peptidic alpha-helix. Such coil repeat may include the repeat of identical motifs, or of different (e.g. variant) motifs, which are functional by recognizing a matching motif to assemble at least two peptidic alpha-helices with high affinity.

Functionally active variants may be obtained by sequence alterations in the peptide sequence e.g., by one or more point mutations, wherein the sequence alterations substantially retains a function of the unaltered peptide sequence. Such sequence alterations or point mutations can include, but are not limited to, (conservative) substitutions, additions, deletions, mutations and insertions, e.g. the alteration of 1, 2, 3, or 4 amino acids, or by addition or insertion of one to several amino acids, e.g. 1, 2, 3, or 4 amino acids, or by a chemical derivatization of one to several amino acids, e.g. 1, 2, 3, or 4, or combination thereof, preferably by point mutations that are not contiguous. The substitutions in amino acid residues may be conservative substitutions, for example, substituting one hydrophobic amino acid for an alternative hydrophobic amino acid.

Conservative substitutions are those that take place within a family of amino acids that are related in their side chains and chemical properties. Examples of such families are amino acids with basic side chains, with acidic side chains, with non-polar aliphatic side chains, with non-polar aromatic side chains, with uncharged polar side chains, with small side chains, with large side chains etc.

Preferred point mutations refer to the exchange of amino acids of the same polarity and/or charge. In this regard, amino acids refer to twenty naturally occurring amino acids encoded by sixty-four triplet codons. These 20 amino acids can be split into those that have neutral charges, positive charges, and negative charges:

The "neutral" amino acids are shown below along with their respective three-letter and single-letter code and polarity:
Alanine: (Ala, A) nonpolar, neutral;
Asparagine: (Asn, N) polar, neutral;
Cysteine: (Cys, C) nonpolar, neutral;
Glutamine: (Gln, Q) polar, neutral;
Glycine: (Gly, G) nonpolar, neutral;
Isoleucine: (Ile, I) nonpolar, neutral;
Leucine: (Leu, L) nonpolar, neutral;
Methionine: (Met, M) nonpolar, neutral;
Phenylalanine: (Phe, F) nonpolar, neutral;
Proline: (Pro, P) nonpolar, neutral;
Serine: (Ser, S) polar, neutral;
Threonine: (Thr, T) polar, neutral;
Tryptophan: (Trp, W) nonpolar, neutral;
Tyrosine: (Tyr, Y) polar, neutral;
Valine: (Val, V) nonpolar, neutral; and
Histidine: (His, H) polar, positive (10%) neutral (90%).
The "positively" charged amino acids are:
Arginine: (Arg, R) polar, positive; and
Lysine: (Lys, K) polar, positive.
The "negatively" charged amino acids are:
Aspartic acid: (Asp, D) polar, negative; and
Glutamic acid: (Glu, E) polar, negative.

Specifically, functional variants of a motif may include point mutations i.e., the insertion, deletion or substitution of 1 or 2 amino acids, in particular those which are conservative substitutions. Thereby, the coiled coil hydrophobic residue periodicity can be maintained.

The term "peptidic alpha-helix" as used herein shall mean the alpha-helix structure based on a peptide sequence comprising a number of motif repeats, herein referred to as coil repeats. Such alpha-helix is capable of binding to one or more peptidic counterpart alpha-helices, also called matching alpha-helices to form a dimer, trimer or further oligomer, also called coiled coil (by longitudinal assembly or self-assembly of the matching alpha-helices).

A coiled coil is a structural motif in polypeptides or peptides, in which two to seven alpha-helices are coiled together like the strands of a rope. In some embodiments, the coiled coil is one with two alpha-helices coiled together. Such alpha helical regions are likely to form coiled-coil structures and may be involved in oligomerization of the coil repeats as measured in a suitable coiled coil interaction binding assay.

Specifically, a dimer of alpha-helices can be formed by contacting two monomers, such that the dimer is formed through an interaction with the two alpha helix coiled coil domains.

According to a specific example, the coils comprise a heptad peptide e.g., with the amino acid sequence as set forth in SEQ ID NO: 7 or 8 (coil and anti-coil), which include n repeats, wherein n=3-5.

The assembly of two matching peptidic alpha-helices is understood as a "coiled coil", and the connector composed a coiled coil, or an assembly of at least two polypeptide chains connected by a coiled coil is understood as comprising a helical coiled coil-type structure.

The term "terminal region" with respect to an amino acid sequence shall mean the C-terminal region, the N-terminal region, or both. The terminal region of a polypeptide (which term is herein understood as referring to both, a polypeptide or protein) sequence is specifically understood as the region of consecutive amino acids including the terminal amino acid, such region including e.g., the peptidic alpha-helix part of the polypeptide. Typically, the terminal region including or consisting of the peptidic alpha-helix includes or consists of at least 15, 20, 25, 30, 35, 40, 45, or 50 consecutive amino acids including the terminal amino acid (i.e., the terminus), e.g., preferably a number of amino acids ranging between 20 and 45 amino acids. For example, with reference to the terminal region including 5 repeats of a heptad motif, the terminal region includes 35 consecutive amino acids including the terminal amino acid.

When the peptidic alpha-helix is positioned in a non-terminal region, the polypeptide sequence comprises the peptidic alpha-helix as consecutive amino acid sequence incorporated into the polypeptide sequence, however, not including a terminal amino acid, in particular not including a terminal region of at least 5, 10, 15, 20, 25, or 35 amino acids.

The term "multimeric protein" is herein understood as a composite protein, which is composed of at least two polypeptide chains, and optionally one or more further components which may be of peptidic structure or otherwise (e.g., non-peptidic or non-polypeptide). Specifically, the multimeric protein is a proteinaceous construct, which comprises two peptides or polypeptides (dimer e.g., homodimer or heterodimer), or three peptides or polypeptides (trimer e.g., homotrimer or heterotrimer), or four peptides or polypeptides (tetramer e.g., homotetramer or heterotetramer).

Herein the term "polypeptide" is understood to refer to both, polypeptides and proteins, and the term "protein" shall always include polypeptides. The term "peptide" shall include an amino acid sequence with a length of 2-50 amino acids, in particular 5-40 amino acids.

The multimeric protein can be a vaccine component, which is composed of at least one vaccine antigen or immunogen (in particular a peptide immunogen) and an adjuvant.

The term "immunogen" as used herein shall mean one or more antigens triggering an immune response in a subject. The term "antigen" as used herein shall in particular refer to any antigenic determinant, which can be possibly recognized by a binding site of an antibody or is able to bind to the peptide groove of HLA class I or class II molecules and as such may serve as stimulant for specific T cells. The target antigen is either recognized as a whole target molecule or as a fragment of such molecule, especially substructures, e.g. a polypeptide or carbohydrate structure of targets, generally referred to as "epitopes", e.g. B-cell epitopes, T-cell epitope), which are immunologically relevant, i.e. are also recognizable by natural or monoclonal antibodies. Herein the use of T cell epitopes is preferred, e.g. to provide for allergy vaccines.

The term "peptide immunogen" as used herein shall mean an antigen or immunogen of peptidic structure, in particular an immunogen that comprises or consists of a peptide of a specific amino acid sequence, which is either provided as a linear peptide or branched peptide, comprising naturally-occurring amino acid residues or modified ones, e.g. a derivative obtained by modification or chemical derivatization, such as by phosphorylation, methylation, acetylation, amidation, formation of pyrrolidone carboxylic acid, isomerization, hydroxylation, sulfation, flavin-binding, cysteine oxidation and nitrosylation.

The peptide immunogen is specifically designed to trigger an immune response in a subject, and particularly includes one or more antigenic determinants, which can be possibly recognized by a binding site of an antibody or is able to bind to the peptide groove of HLA class I or class II molecules or other antigen presenting molecules such as CD1 and as such may serve as stimulant for specific T cells. The target antigen is either recognized as a whole target molecule or as a fragment of such molecule, especially substructures, e.g. a polypeptide or carbohydrate structure of targets, generally referred to as "epitopes", e.g. B-cell epitopes, T-cell epitope, which are immunologically relevant, i.e. are also recognizable by natural or monoclonal antibodies. Herein the use of B cell epitopes is preferred to provide for e.g. oncology vaccines.

The term "epitope" as used herein shall in particular refer to a molecular structure which may completely make up a specific binding partner or be part of a specific binding partner to a binding site of modular antibody of the present invention. The term epitope may also refer to haptens. Chemically, an epitope may either be composed of a carbohydrate, a peptide, a fatty acid, an organic, biochemical or inorganic substance or derivatives thereof and any combinations thereof. If an epitope is a polypeptide, it will usually include at least 3 amino acids, preferably at least 4, 5, 6, 7, 8, 9, 10, 11, 12 or 13 amino acids. There is no critical upper limit to the length of the peptide, which could comprise nearly the full length of a polypeptide sequence of a protein. Epitopes can be either linear or conformational epitopes. A linear epitope is comprised of a single segment of a primary sequence of a polypeptide or carbohydrate chain. Linear epitopes can be contiguous or overlapping. Conformational epitopes are comprised of amino acids or carbohydrates brought together by folding of the polypeptide to form a tertiary structure and the amino acids are not necessarily adjacent to one another in the linear sequence. Specifically, epitopes are at least part of diagnostically relevant molecules, i.e. the absence or presence of an epitope in a sample is qualitatively or quantitatively correlated to either a disease or to the health status of a patient or to a process status in manufacturing or to environmental and food status. Epitopes may also be at least part of therapeutically relevant molecules, i.e. molecules which can be targeted by the specific binding domain which changes the course of the disease.

In cancer disease an immune response to a self-antigen is desirable. The term "self-antigen" as used herein means any antigen, specifically polypeptide or peptide produced by a normal, healthy subject that does not elicit an immune response as such. These self-antigens may be produced at aberrant or high levels in certain disease states, including cancer disease, so called tumour associated antigens (TAAs). Self-antigens which are associated with auto-immune disease are herein called auto-antigens.

It is understood that the self-antigens can be naturally occurring, recombinantly or synthetically produced. It is also understood that the self-antigens need not be identical to the naturally produced antigen, but rather can include variations thereto having certain sequence identities, similarities or homology.

The choice of the self-antigen for use in cancer therapy depends on the type and stage of the cancer disease, and in particular on the expression pattern of a cancer cell such as derived from a tumour or metastases. Specific examples of selected tumour associated antigens possibly used in a vaccine as described herein are Epithelial cell adhesion molecule (EpCAM), Lewis Y, alphafetoprotein (AFP) and carcinoembryonic antigen (CEA), HER2/neu, MUC-1, etc.

The choice of an auto-antigen for use in the therapy of auto-immune diseases depends on the type of the auto-immune disease. Specific examples of selected auto-immune disease associated antigens possibly used in a vaccine as described herein are C1q, ADAMTS13, Desmogelin 3, keratin, gangliosides (e.g. GM1, GD1a, GQ1b), collagen type IV, IgM, cardiolipin, annexin A5, etc.

In some embodiments, the immunogen comprises one or more specific allergens. An "allergen" is an antigen which can initiate a state of hypersensitivity, or which can provoke an immediate hypersensitivity reaction in a subject already sensitized with the allergen. Allergens are commonly proteins or chemicals bound to proteins which have the property of being allergenic. However, allergens can also include organic or inorganic materials derived from a variety of synthetic or natural sources such as plant materials, metals, ingredients in cosmetics or detergents, latexes, or the like.

The choice of an allergen for use in the anti-allergy therapy depends on the type and severity of allergy. Specific examples of selected allergy associated antigens possibly used in a vaccine as described herein are any allergen conventionally used as immunogen, specifically house dust mite allergens (e.g. Der p1, Der p2, Der p3/-Der p23, Der f1, Der f2, Derf3/-Der f23), cat dander, grass or tree pollen, cockroach allergens, etc.

The choice of an antigen specifically inducing immune response against a pathogen for use in the prophylaxis or therapy of infectious diseases depends on the type of the pathogen, e.g. a microbial or viral infectious agent. Specific examples of selected pathogen derived antigens possibly used in a vaccine as described herein are hepatitis B, hepatitis C, Cholera, HIV, Pertussis, Influenza, Typhoid, etc.

A vaccine adjuvant is herein understood as a vaccine component which is capable of enhancing the effectiveness of the vaccine to trigger an immune response against the vaccine antigen.

An enhanced Th1 immune response may include an increase in one or more of the cytokines associated with a Th1 immune response (such as IFNγ), and an increase in activated macrophages.

An enhanced Th1 immune response may include one or more of an increase in antigen specific IgG antibodies, especially IgG1 antibodies.

For example, a vaccine may be provided which includes an immunogenic composition, i.e. an adjuvant component, such as an anti-CD32 moiety (such as a peptide, or an antibody, antibody fragment or construct comprising the antigen-binding site of an antibody, each specifically recognizing CD32) linked to a TLR9 ligand and the first peptidic alpha-helix, and an immunogen component, e.g. comprising a peptide immunogen linked to the second peptidic alpha-helix that matches the first one. Specific examples of such immunogenic compositions are disclosed in WO2014009209A2.

The multimeric protein may be antigen binding molecule such as an antibody, or a fragment thereof.

The term "antibody" as used herein shall refer to polypeptides or proteins that consist of or comprise antibody domains, which are understood as constant and/or variable domains of the heavy and/or light chains of immunoglobulins, with or without a linker sequence. Polypeptides are understood as antibody domains, if comprising a beta-barrel structure consisting of at least two beta-strands of an antibody domain structure connected by a loop sequence. Antibody domains may be of native structure or modified by mutagenesis or derivatization, e.g. to modify the antigen binding properties or any other property, such as stability or functional properties, such as binding to the Fc receptors FcRn and/or Fcgamma receptor.

The antibody as used herein has a specific binding site to bind one or more antigens or one or more epitopes of such antigens, specifically comprising a CDR binding site of a single variable antibody domain, such as VH, VL or VHH, or a binding site of pairs of variable antibody domains, such as a VL/VH pair, an antibody comprising a VL/VH domain pair and constant antibody domains, such as Fab, F(ab'), (Fab)$_2$, scFv, Fv, or a full length antibody.

The term "antibody" as used herein shall particularly refer to antibody formats comprising or consisting of single variable antibody domain, such as VH, VL or VHH, or combinations of variable and/or constant antibody domains with or without a linking sequence or hinge region, including pairs of variable antibody domains, such as a VL/VH pair, an antibody comprising or consisting of a VL/VH domain pair and constant antibody domains, such as heavy-chain antibodies, Fab, F(ab'), (Fab)$_2$, scFv, Fd, Fv, or a full-length antibody, e.g. of an IgG type (e.g., an IgG1, IgG2, IgG3, or IgG4 sub-type), IgA1, IgA2, IgD, IgE, or IgM antibody. The term "full length antibody" can be used to refer to any antibody molecule comprising at least most of the Fc domain and other domains commonly found in a naturally occurring antibody monomer. This phrase is used herein to emphasize that a particular antibody molecule is not an antibody fragment.

The term "antibody" shall particularly apply to antibodies of animal origin, including human species, such as mammalian, including e.g., human, murine, or rabbit, which term shall include recombinant antibodies which are based on a sequence of animal origin, e.g. human sequences.

The term "antibody" further applies to chimeric antibodies with sequences of origin of different species, such as sequences of murine and human origin.

The term "chimeric" as used with respect to an antibody refers to those antibodies wherein one portion of each of the amino acid sequences of heavy and light chains is homologous to corresponding sequences in antibodies derived from a particular species or belonging to a particular class, while the remaining segment of the chain is homologous to corresponding sequences in another species or class. Typically the variable region of both light and heavy chains mimics the variable regions of antibodies derived from one species of mammals, while the constant portions are homologous to sequences of antibodies derived from another. For example, the variable region can be derived from presently known sources using readily available B-cells or hybridomas from non-human host organisms in combination with constant regions derived from, for example, human cell preparations.

The term "antibody" may further apply to humanized antibodies.

The term "humanized" as used with respect to an antibody refers to a molecule having an antigen binding site that is substantially derived from an immunoglobulin from a non-human species, wherein the remaining immunoglobulin structure of the molecule is based upon the structure and/or sequence of a human immunoglobulin. The antigen binding site may either comprise complete variable domains fused onto constant domains or only the complementarity determining regions (CDR) grafted onto appropriate framework regions in the variable domains. Antigen-binding sites may be wild-type or modified, e.g. by one or more amino acid substitutions, preferably modified to resemble human immunoglobulins more closely. Some forms of humanized antibodies preserve all CDR sequences (for example a humanized mouse antibody which contains all six CDRs from the mouse antibody). Other forms have one or more CDRs which are altered with respect to the original antibody.

The term "antibody" further applies to human antibodies.

The term "human" as used with respect to an antibody, is understood to include antibodies having variable and constant regions derived from human germline immunoglobulin sequences. The human antibody of the invention may include amino acid residues not encoded by human germline immunoglobulin sequences (e.g., mutations introduced by random or site-specific mutagenesis in vitro or by somatic mutation in vivo), for example in the CDRs. Human antibodies include antibodies isolated from human immunoglobulin libraries or from animals transgenic for one or more human immunoglobulin.

The term "antibody" specifically applies to antibodies of any class or subclass. Depending on the amino acid sequence of the constant domain of their heavy chains, antibodies can be assigned to the major classes of antibodies IgA, IgD, IgE, IgG, and IgM, and several of these may be further divided into subclasses (isotypes), e.g., IgG1, IgG2, IgG3, IgG4, IgA1, and IgA2.

The term further applies to monoclonal or polyclonal antibodies, specifically a recombinant antibody, which term includes all antibodies and antibody structures that are prepared, expressed, created or isolated by recombinant means, such as antibodies originating from animals, e.g. mammalians including human, that comprises genes or sequences from different origin, e.g. murine, chimeric, humanized antibodies, or hybridoma derived antibodies. Further examples refer to antibodies isolated from a host cell transformed to express the antibody, or antibodies isolated from a recombinant, combinatorial library of antibodies or antibody domains, or antibodies prepared, expressed, created or isolated by any other means that involve splicing of antibody gene sequences to other DNA sequences.

It is understood that the term "antibody" also refers to derivatives of an antibody, in particular functionally active derivatives. An antibody derivative is understood as any combination of one or more antibody domains or antibodies and/or a fusion protein, in which any domain of the antibody may be fused or otherwise connected at any position of one or more other proteins, such as other antibodies, e.g. a binding structure comprising CDR loops, a receptor polypeptide, but also ligands, scaffold proteins, enzymes, toxins and the like. A derivative of the antibody may be obtained by association (e.g. through a connector as described herein) or binding to other substances by various chemical techniques such as covalent coupling, electrostatic interaction, di-sulphide bonding etc. The other substances bound to the antibody may be lipids, carbohydrates, nucleic acids, organic and inorganic molecules or any combination thereof (e.g. PEG, prodrugs or drugs). In a specific embodiment, the antibody is a derivative comprising an additional tag allowing specific interaction with a biologically acceptable compound. There is not a specific limitation with respect to the tag usable in the present invention, as far as it has no or tolerable negative impact on the binding of the antibody to its target. Examples of suitable tags include His-tag, Myc-tag, FLAG-tag, Strep-tag, Calmodulin-tag, GST-tag, MBP-tag, and S-tag. In another specific embodiment, the antibody is a derivative comprising a label. The term "label" as used herein refers to a detectable compound or composition which is conjugated directly or indirectly to the antibody so as to generate a "labeled" antibody. The label may be detectable by itself, e.g. radioisotope labels or fluorescent labels, or, in the case of an enzymatic label, may catalyze chemical alteration of a substrate compound or composition which is detectable.

According to a specific example, the multimeric protein is an antibody construct which is composed of at least two polypeptide chains that are connected to each other by the connector as described herein. Specific examples include constructs wherein at least one antibody domain (either a single domain or a chain of 2, 3, or 4 antibody domains) is connected to another antibody domain (either a single domain or a chain of 2, 3, or 4 antibody domains), such as single chain antibody constructs wherein the linker is replaced by the connector as described herein, or constructs comprising an antibody heavy and light chain connected by a connector as described herein.

The components of the connector or the multimeric protein as described herein, or parts thereof with or without the coil repeats may be obtained by various methods known in the art, e.g. by purification or isolation from cell culture, recombinant technology or by chemical synthesis.

As used herein, the term "recombinant" refers to a molecule or construct that does not naturally occur in a host cell. In some embodiments, recombinant nucleic acid molecules contain two or more naturally-occurring sequences that are linked together in a way that does not occur naturally. A recombinant protein refers to a protein that is encoded and/or expressed by a recombinant nucleic acid. In some embodiments, "recombinant cells" express genes that are not found in identical form within the native (i.e., non-recombinant) form of the cell and/or express native genes that are otherwise abnormally over-expressed, under-expressed, and/or not expressed at all due to deliberate human intervention. Recombinant cells contain at least one recombinant polynucleotide or polypeptide. "Recombination", "recombining", and generating a "recombined" nucleic acid generally encompass the assembly of at least two nucleic acid fragments. In certain embodiments, recombinant proteins and recombinant nucleic acids remain functional, i.e., retain their activity or exhibit an enhanced activity in the host cell.

Thus, the invention further refers to the production of the connector or the mkultimeric protein comprising the connector, or components thereof (e.g. any of the polypeptide chains, in particular the first alpha-helix or the first polypeptide chain comprising the first alpha-helix), and the recombinant means for such production, including a nucleic acid encoding the respective amino acid sequence, an expression cassette, a vector or plasmid comprising the nucleic acid encoding the amino acid sequence to be expressed, and a host cell comprising any such means. Suitable standard recombinant DNA techniques are known in the art and described inter alia in Sambrook et al., "Molecular Cloning: A Laboratory Manual" (1989), 2nd Edition (Cold Spring Harbor Laboratory press).

The multimeric protein as described herein is specifically composed of at least one heterologous recombinant polypeptide chain, produced in a eukaryotic cell, preferably any of the mammalian or yeast cells as described herein, preferably as secreted proteins.

The term "heterologous" as used herein with respect to a nucleotide or amino acid sequence or protein, refers to a compound which is either foreign, i.e. "exogenous", such as not found in nature, to a given host cell; or that is naturally found in a given host cell, e.g., is "endogenous", however, in the context of a heterologous construct, e.g. employing a heterologous nucleic acid. The heterologous nucleotide sequence as found endogenously may also be produced in an unnatural, e.g. greater than expected or greater than naturally found, amount in the cell. The heterologous nucleotide sequence, or a nucleic acid comprising the heterologous nucleotide sequence, possibly differs in sequence from the endogenous nucleotide sequence but encodes the same protein as found endogenously. Specifically, heterologous nucleotide sequences are those not found in the same relationship to a host cell in nature. Any recombinant or artificial nucleotide sequence is understood to be heterologous. An example of a heterologous polynucleotide is a nucleotide sequence not natively associated with a promoter used in an expression construct, e.g. to obtain a hybrid promoter, or operably linked to a coding sequence, as described herein. As a result, a hybrid or chimeric polynucleotide may be obtained. A further example of a heterologous compound is a protein encoding polynucleotide operably linked to a transcriptional control element, e.g., an exogenous promoter to which an endogenous, naturally-occurring protein coding sequence is not normally operably linked.

The term "host cell" as used herein shall refer to primary subject cells transformed to produce a particular recombinant protein, such as a multimeric protein as described herein or one or more polypeptide chains of any such multimeric protein, and any progeny thereof. It should be understood that not all progeny are exactly identical to the parental cell (due to deliberate or inadvertent mutations or differences in environment), however, such altered progeny are included in these terms, so long as the progeny retain the same functionality as that of the originally transformed cell. The term "host cell line" refers to a cell line of host cells as used for expressing a recombinant gene to produce recombinant polypeptides such as recombinant antibodies. The term "cell line" as used herein refers to an established clone of a particular cell type that has acquired the ability to proliferate over a prolonged period of time. Such host cell or host cell line may be maintained in cell culture and/or cultivated to produce a recombinant polypeptide.

According to a specific aspect, a recombinant construct is obtained by ligating the relevant genes into a vector. These genes can be stably integrated into a host cell genome by transforming the host cell using such vectors. The polypeptides encoded by the genes can be produced using the recombinant host cell line by culturing a transformant, thus obtained in an appropriate medium, isolating the expressed protein from the culture, and purifying it by a method appropriate for the expressed product, in particular to separate the protein from contaminating proteins.

For recombinant technologies, isolated nucleic acids may be provided.

With reference to nucleic acids as described herein, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism. When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An "isolated nucleic acid" (either DNA or RNA) may further represent a molecule produced directly by biological or synthetic means and separated from other components present during its production.

With reference to polypeptides or proteins, the term "isolated" shall specifically refer to compounds that are free or substantially free of material with which they are naturally associated such as other compounds with which they are found in their natural environment, or the environment in which they are prepared (e g. cell culture) when such preparation is by recombinant DNA technology practiced in vitro or in vivo. Isolated compounds can be formulated with diluents or adjuvants and still for practical purposes be isolated—for example, the polypeptides or polynucleotides can be mixed with pharmaceutically acceptable carriers or excipients when used in diagnosis or therapy.

As isolation and purification methods for obtaining a recombinant polypeptide or protein product, methods, such as methods utilizing difference in solubility, such as salting out and solvent precipitation, methods utilizing difference in molecular weight, such as ultrafiltration and gel electrophoresis, methods utilizing difference in electric charge, such as ion-exchange chromatography, methods utilizing specific affinity, such as affinity chromatography, methods utilizing difference in hydrophobicity, such as reverse phase high performance liquid chromatography, and methods utilizing difference in isoelectric point, such as isoelectric focusing may be used.

The highly purified product is essentially free from contaminating proteins, and preferably has a purity of at least 90%, more preferred at least 95%, or even at least 98%, up to 100%. The purified products may be obtained by purification of the cell culture supernatant or else from cellular debris.

As isolation and purification methods the following standard methods are preferred: Cell disruption (if a protein is obtained intracellularly), cell (debris) separation and wash by Microfiltration or Tangential Flow Filter (TFF) or centrifugation, protein purification by precipitation or heat treatment, protein activation by enzymatic digest, protein purification by chromatography, such as ion exchange (IEX), hydrophobic ointeraction chromatography (HIC), Affinity chromatography, size exclusion (SEC) or HPLC Chromatography, protein precipitation of concentration and washing by ultrafiltration steps.

The isolated and purified proteins can be identified by conventional methods such as Western blot, HPLC, activity assay, or ELISA.

Therefore, the invention particularly provides for improved connector domains and improved multimeric proteins wherein polypeptide chains are connected to each other using such improved connectors.

According to a specific example, the loss of C-terminal Lys in proteins produced in mammalian cells could be avoided and a correct C-terminus (Lys-extension e.g., an additional Ala, Gly or Ser after a C-terminal Lys) was obtained. Such correct terminus surprisingly not only stabilized the protein construct through a stabilized coiled coil structure but also enhanced the affinity of connecting the coil to the counter coil.

The foregoing description will be more fully understood with reference to the following examples. Such examples are, however, merely representative of methods of practicing one or more embodiments of the present invention and should not be read as limiting the scope of invention.

EXAMPLES

Example 1: Improved ScFV-coil1

An immunogenic composition is prepared according to WO2014009209A2. Therefore, ScFV-coil1 is the basis for the preparation of warhead. In order to transform a ScFV-coil1 molecule into a warhead molecule, CpG oligonucleotides (TLR9 binder) are coupled to "Lys" amino acids in the ScFV-coil1 protein backbone.

According to prior art, ScFV-coil1 was produced in mammalian cells such as CAP-T cells, HEK293 and CHO cells but also in insect cells such as S2 cells and in yeast cells (*Pichia pastoris*).

As an exemplary ScFV-coil1, a polypeptide characterized by the amino acid sequence, identified as SEQ ID 49 (FIG. 1), has been used.

However, an analysis in mass spectrometry showed that in ~40% of the ScFV-coil1 molecules produced in mammalian cells, the Lys(289) was cleaved off (FIG. 4a), a phenomenon which has previously been described by Harris (1995. Processing of C-terminal lysine and arginine residues of proteins isolated from mammalian cell culture. *J. Chromatogr. A* 705:129-134). However, ScFV-coil1 produced in insect cells did not show this phenomenon as 100% of the molecules contained the Lys(289) (FIG. 4b). The Lys molecules in the ScFV-coil1 are targets for coupling of the CpG molecules and therefore important for the full functionality of ScFV-coil1 in the immunogenic construct.

As a solution to this problem, the following was constructed:

By adding an Ala to the C'-end of the sequence (ScFV-coil1ala, FIG. 2) Lys(289) was effectively protected. Mass spectrometry of ScFV-coil1ala produced in HEK293 cells or in CHO cells showed 100% full length ScFV-coil1ala (FIG. 4c). The same was true when Gly or Ser were added at the C'-end (data not shown).

According to this example, ScFV-coil1 (the basis for the warhead) contains a 5× heptad repeat structure (pepE, italic in FIGS. 1 and 2) which forms a coiled coil interaction with a similar 5× heptad repeat structure called pepK (FIG. 3), which is part of the immunogen component. When immunogen and warhead are mixed, a coiled coil is formed, thus, coupling warhead and immunogen with high affinity to form a stable complex to be used to produce a vaccine construct for use in allergy, oncology, infectious diseases and/or autoimmune diseases. The immunogen component would need to further comprise one or more relevant epitopes to trigger an effective immune response as necessary to treat any such disease.

When scFV-coil1 and ScFV-coil1ala were compared in Octet analyses for the affinity between the pepE and pepK, the affinity between pepK and scFV-coil1 was lower than the affinity between pepK and scFV-coil1ala, whereas the $K_D$ value obtained with the partly truncated version of ScFV-coil1 was higher (reflecting a lower affinity) than that of the full length (FIG. 5). Affinity was similarly increased with Gly or Ser at the C'-end (data not shown).

Example 2: Mass Spectrometry of ScFV-Coil1 Variants

Purified ScFV-coil1 variants were analyzed for mass distribution on a Waters 3100 Mass Detector according to the manufacturer's instructions. Mass spectra were acquired by electrospray ionization (ESI-MS) operating in positive ion mode. The mass spectra were de-convoluted by the program MaxEnt v. 4.1 (Waters).

The expected molecular weight (MW) based on the sequence of FIG. 1 is 30764 Da.

As shown in FIG. 4A, for scFV-coil1 produced in recombinant HEK293 cells, the MW found are 30755.5 Da (~60% of total material) and 30630 Da (~40% of total material) which corresponds to expected MW minus Lys(289)

As shown in FIG. 4B, for scFV-coil1 produced in recombinant S2 insect cells cells, the MW found is 30755.5 Da indicating full length protein.

The expected molecular weight (MW) based on the sequence of FIG. 2 is 30835.4 Da.

As shown in FIG. 4C, for scFV-coil1ala (obtained according to Example 1) produced in recombinant HEK293 cells, the MW found is 30831.0 Da indicating full length protein.

Example 3: Affinity Analyses of pepK and scFV-Coil1 or ScFV-Coil1ala

The affinity of the E-coil on the C-terminus of the different versions of ScFV-coil1 for the pepK was determined by Bio-Layer Interferometry on an Octet QK instrument. For this purpose Streptavidin-biosensors were loaded with biotinylated pepK, and after blocking the surface for unspecific binding, association and dissociation rates were measured for the ScFV-coil1 proteins. From the binding curves obtained by different protein concentrations the affinities were calculated. For clarity, only one concentration is shown in the graph. $K_D$ values of 8.7 pM for ScFV-coil1ala (obtained according to Example 1) obtained from recombinant HEK cells, 15.8 pM for ScFV-coil1 obtained from recombinant S2 insect cells, and 32.5 pM for ScFV-coil1 obtained from recombinant HEK cells, were calculated. The lowest affinity is found for the ScFV-coil1 derived from the HEK cells which show deletion of the Lys 289 in ~40% of molecules (FIG. 4A). Material from insect cells which contains the complete original sequence (FIG. 4B) shows an intermediate affinity, whereas the ScFv-coil1ala (FIG. 4C) unexpectedly shows the highest affinity, see FIG. 5.

The invention claimed is:

1. A multimeric protein comprising a first polypeptide and a second polypeptide joined by a connector, the connector consisting of a coiled coil-type structure consisting of a first peptidic alpha-helix and a second peptidic alpha-helix, wherein the first and the second peptidic alpha-helices form the coiled coil-type structure,
wherein:
  i) the first peptidic alpha-helix consists of repeats of the amino acid motif a-$x_1$ and a C-terminal motif a-$x_1$-$x_2$, and the second peptidic alpha helix consists of repeats of an amino acid motif $x_1$-a selected from the group consisting of SEQ ID NOs: 2, 4, 6, and 8, wherein the first polypeptide of the multimeric protein is fused to the N-terminus of the first peptidic alpha-helix, and the second polypeptide of the multimeric protein is fused to the N-terminus or to the C-terminus of the second peptidic alpha-helix; or
  ii) the first peptidic alpha-helix consists of an N-terminal motif $x_2$-$x_1$-a and repeats of the amino acid motif $x_1$-a, and the second alpha-helix consists of repeats of an amino acid motif a-$x_1$ selected from the group consisting of SEQ ID NOs: 1, 3, 5, and 7, wherein the first polypeptide of the multimeric protein is fused to the C-terminus of the first peptidic alpha-helix, and the second polypeptide of the multimeric protein is fused to the N-terminus or to the C-terminus of the second peptidic alpha-helix;
wherein in the first peptidic alpha-helix:
  a1) the repeating motif a-$x_1$ is SEQ ID NO:1 and the C-terminal motif a-$x_1$-$x_2$ is SEQ ID NO:1 with a C-terminal extension $x_2$ consisting of 1-2 amino acids;
  a2) the repeating motif a-$x_1$ is SEQ ID NO:1 and the C-terminal motif a-$x_1$-$x_2$ is SEQ ID NO:41, SEQ ID NO:69, or SEQ ID NO:71;
  b1) the repeating motif a-$x_1$ is SEQ ID NO:3 and the C-terminal motif a-$x_1$-$x_2$ is SEQ ID NO:3 with a C-terminal extension $x_2$ consisting of 1-2 amino acids;
  b2) the repeating motif a-$x_1$ is SEQ ID NO:3 and the C-terminal motif a-$x_1$-$x_2$ is SEQ ID NO:43, SEQ ID NO:85, or SEQ ID NO:87;
  c1) the repeating motif a-$x_1$ is SEQ ID NO:5 and the C-terminal motif a-$x_1$-$x_2$ is SEQ ID NO:5 with a C-terminal extension $x_2$ consisting of 1-2 amino acids;
  c2) the repeating motif a-$x_1$ is SEQ ID NO:5 and the C-terminal motif a-$x_1$-$x_2$ is SEQ ID NO:45, SEQ ID NO:101, or SEQ ID NO:103;
  d1) the repeating motif a-$x_1$ is SEQ ID NO:7 and the C-terminal motif a-$x_1$-$x_2$ is SEQ ID NO:7 with a C-terminal extension $x_2$ consisting of 1-2 amino acids;
  d2) the repeating motif a-$x_1$ is SEQ ID NO:7 and the C-terminal motif a-$x_1$-$x_2$ is SEQ ID NO:47, SEQ ID NO:117, or SEQ ID NO:119;
  e1) the repeating motif $x_1$-a is SEQ ID NO:2 and the N-terminal motif $x_2$-$x_1$-a is SEQ ID NO:2 with an N-terminal extension $x_2$ consisting of 1-2 amino acids;
  e2) the repeating motif $x_1$-a is SEQ ID NO:2 and the N-terminal motif $x_2$-$x_1$-a is SEQ ID NO:42, SEQ ID NO:77, or SEQ ID NO:79;
  f1) the repeating motif $x_1$-a is SEQ ID NO:4 and the N-terminal motif $x_2$-$x_1$-a is SEQ ID NO:4 with an N-terminal extension $x_2$ consisting of 1-2 amino acids;
  f2) the repeating motif $x_1$-a is SEQ ID NO:4 and the N-terminal motif $x_2$-$x_1$-a is SEQ ID NO:44, SEQ ID NO:93, or SEQ ID NO:95;
  g1) the repeating motif $x_1$-a is SEQ ID NO:6 and the N-terminal motif $x_2$-$x_1$-a is SEQ ID NO:6 with an N-terminal extension $x_2$ consisting of 1-2 amino acids;
  g2) the repeating motif $x_1$-a is SEQ ID NO:6 and the N-terminal motif $x_2$-$x_1$-a is SEQ ID NO:46, SEQ ID NO:109, or SEQ ID NO:111;
  h1) the repeating motif $x_1$-a is SEQ ID NO:8 and the N-terminal motif $x_2$-$x_1$-a is SEQ ID NO:8 with an N-terminal extension $x_2$ consisting of 1-2 amino acids; or
  h2) the repeating motif $x_1$-a is SEQ ID NO:8 and the N-terminal motif $x_2$-$x_1$-a is SEQ ID NO:48, SEQ ID NO:125, or SEQ ID NO:127.

2. The multimeric protein of claim 1, wherein at least one of the 1-2 amino acids of $x_2$ is selected from the group consisting of Alanine, Glycine, Serine, Isoleucine, Leucine, Phenylalanine, Valine, and Proline.

3. The multimeric protein of claim 2, wherein $x_2$ consists of two amino acids, and the first amino acid is selected from the group consisting of Alanine, Glycine, Serine, Isoleucine, Leucine, Phenylalanine, Valine, and Proline.

4. The multimeric protein of claim 1, wherein the number of repeating amino acid motifs in each of said first and second alpha-helices is 2-9.

5. The multimeric protein of claim 1, wherein the first and second alpha-helices are parallel or anti-parallel alpha-helices.

6. The multimeric protein of claim 1, comprising a heterodimeric coiled-coil, wherein the repeating amino acid motif in the first alpha-helix is different from the repeating amino acid motif in the second alpha-helix.

7. The multimeric protein of claim 1, wherein $x_2$ consists of 1 amino acid.

8. The multimeric protein of claim 7, wherein the amino acid is any of Alanine, Glycine, or Serine.

9. The multimeric protein of claim 1, wherein the first and second polypeptide are independently selected from the group consisting of:
  a) a vaccine antigen or adjuvant;
  b) an antibody or antibody domain;
  c) an antibody derivative comprising an antibody connected to a label, tag, enzyme, receptor, ligand, toxin, lipid, carbohydrate, or nucleic acid; and
  d) a receptor or receptor ligand connected to a solid phase carrier.

10. A multimeric protein comprising a first polypeptide and a second polypeptide joined by a connector, the connector consisting of a coiled coil-type structure consisting of a first peptidic alpha-helix and a second peptidic alpha-helix, wherein the first and second peptidic alpha-helices form the coiled coil-type structure, wherein:
  i) the first peptidic alpha helix consists of repeats of the amino acid motif a-x1 and a C-terminal motif a-$x_1$-$x_2$, and the second peptidic alpha helix consists of repeats of an amino acid motif $x_1$-a selected from the group consisting of SEQ ID NOs: 2, 4, 6, and 8, wherein the first polypeptide of the multimeric protein is fused to the N-terminus of the first peptidic alpha-helix, and the second polypeptide of the multimeric protein is fused to the N-terminus or to the C-terminus of the second peptidic alpha-helix; or ii) the first peptide alpha helix consists of an N-terminal motif $x_2$-$x_1$-a and repeats of the amino acid motif $x_1$-a, and the second peptidic alpha helix consists of repeats of an amino acid motif a-$x_1$ selected from the group consisting of SEQ ID NOs: 1, 3, 5, and 7, wherein the first polypeptide of the multimeric protein is fused to the C-terminus of the first peptidic alpha-helix, and the second polypeptide of the multimeric protein is fused to the N-terminus or to the C-terminus of the second peptidic alpha-helix;

wherein in the first peptidic alpha-helix:

a1) the repeating motif a-$x_1$ is SEQ ID NO: 1 and the C-terminal motif a-$x_1$-$x_2$ is SEQ ID NO: 1 with a C-terminal extension $x_2$ consisting of 1-2 amino acids;

a2) the repeating motif a-$x_1$ is SEQ ID NO: 1 and the C-terminal motif a-$x_1$-$x_2$ is SEQ ID NO: 41;

b1) the repeating motif a-$x_1$ is SEQ ID NO: 3 and the C-terminal motif a-$x_1$-$x_2$ is SEQ ID NO: 3 with a C-terminal extension x2 consisting of 1-2 amino acids;

b2) the repeating motif a-$x_1$ is SEQ ID NO: 3 and the C-terminal motif a-$x_1$-$x_2$ is SEQ ID NO: 43;

c1) the repeating motif a-x1 is SEQ ID NO: 5 and the C-terminal motif a-$x_1$-x2 is SEQ ID NO: 5 with a C-terminal extension x2 consisting of 1-2 amino acids;

c2) the repeating motif a-$x_1$ is SEQ ID NO: 5 and the C-terminal motif a-$x_1$-$x_2$ is SEQ ID NO: 45;

d1) the repeating motif a-$x_1$ is SEQ ID NO: 7 and the C-terminal motif a-$x_1$-x2 is SEQ ID NO: 7 with a C-terminal extension x2 consisting of 1-2 amino acids;

d2) the repeating motif a-$x_1$ is SEQ ID NO: 7 and the C-terminal motif a-$x_1$-$x_2$ is SEQ ID NO: 47;

e1) the repeating motif $x_1$-a is SEQ ID NO: 2 and the N-terminal motif x2-$x_1$-a is SEQ ID NO: 2 with a N-terminal extension x2 consisting of 1-2 amino acids;

e2) the repeating motif $x_1$-a is SEQ ID NO: 2 and the N-terminal motif $x_2$-$x_1$-a is SEQ ID NO: 42;

f1) the repeating motif $x_1$-a is SEQ ID NO: 4 and the N-terminal motif $x_2$-$x_1$-a is SEQ ID NO: 4 with a N-terminal extension x2 consisting of 1-2 amino acids;

f2) the repeating motif $x_1$-a is SEQ ID NO: 4 and the N-terminal motif $x_2$-$x_1$-a is SEQ ID NO: 44;

g1) the repeating motif $x_1$-a is SEQ ID NO: 6 and the N-terminal motif $x_2$-$x_1$-a is SEQ ID NO: 6 with a N-terminal extension x2 consisting of 1-2 amino acids;

g2) the repeating motif $x_1$-a is SEQ ID NO: 6 and the N-terminal motif x2-x1-a is SEQ ID NO: 46;

h1) the repeating motif $x_1$-a is SEQ ID NO: 8 and the N-terminal motif $x_2$-$x_1$-a is SEQ ID NO: 8 with a N-terminal extension x2 consisting of 1-2 amino acids; or h2) the repeating motif $x_1$-a is SEQ ID NO: 8 and the N-terminal motif $x_2$-$x_1$-a is SEQ ID NO: 48.

11. The multimeric protein of claim 10, wherein at least one of the 1-2 amino acids of $x_2$ is selected from the group consisting of Alanine, Glycine, Serine, Isoleucine, Leucine, Phenylalanine, Valine, and Proline.

12. The multimeric protein of claim 11, wherein $x_2$ consists of two amino acids, and the first amino acid is selected from the group consisting of Alanine, Glycine, Serine, Isoleucine, Leucine, Phenylalanine, Valine, and Proline.

13. The multimeric protein of claim 10, wherein the number of repeating amino acid motifs in each of said first and second alpha-helices is 2-9.

14. The multimeric protein of claim 10, wherein the first and second alpha-helices are parallel or anti-parallel alpha-helices.

15. The multimeric protein of claim 10, comprising a heterodimeric coiled-coil, wherein the repeating amino acid motif in the first alpha-helix is different from the repeating amino acid motif in the second alpha-helix.

16. The multimeric protein of claim 10, wherein $x_2$ consists of 1 amino acid.

17. The multimeric protein of claim 16, wherein the amino acid is any of Alanine, Glycine, or Serine.

* * * * *

SEQUENCE LISTING

<160> NUMBER OF SEQ ID NOS: 131

<210> SEQ ID NO 1
<211> LENGTH: 7
<212> TYPE: PRT
<213> ORGANISM: Artificial Sequence
<220> FEATURE:
<223> OTHER INFORMATION: Motif

<400> SEQUENCE: 1

Glu Ile Ala Ala Leu Glu Lys
1               5

<210> SEQ ID NO 2
<211> LENGTH: 7
<212> TYPE: PRT
<213> ORGANISM: Artificial Sequence
<220> FEATURE:
<223> OTHER INFORMATION: Motif

<400> SEQUENCE: 2

Lys Ile Ala Ala Leu Lys Glu
1               5

<210> SEQ ID NO 3
<211> LENGTH: 7
<212> TYPE: PRT
<213> ORGANISM: Artificial Sequence
<220> FEATURE:
<223> OTHER INFORMATION: Motif

<400> SEQUENCE: 3

Glu Ile Ser Ala Leu Glu Lys
1               5

<210> SEQ ID NO 4
<211> LENGTH: 7
<212> TYPE: PRT
<213> ORGANISM: Artificial Sequence
<220> FEATURE:
<223> OTHER INFORMATION: Motif

<400> SEQUENCE: 4

Lys Ile Ser Ala Leu Lys Glu
1               5

<210> SEQ ID NO 5
<211> LENGTH: 7
<212> TYPE: PRT
<213> ORGANISM: Artificial Sequence
<220> FEATURE:
<223> OTHER INFORMATION: Motif

<400> SEQUENCE: 5

Glu Val Ala Ala Leu Glu Lys
1               5

<210> SEQ ID NO 6
<211> LENGTH: 7
<212> TYPE: PRT
<213> ORGANISM: Artificial Sequence
<220> FEATURE:
<223> OTHER INFORMATION: Motif

```
<400> SEQUENCE: 6

Lys Val Ala Ala Leu Lys Glu
1               5

<210> SEQ ID NO 7
<211> LENGTH: 7
<212> TYPE: PRT
<213> ORGANISM: Artificial Sequence
<220> FEATURE:
<223> OTHER INFORMATION: Motif

<400> SEQUENCE: 7

Glu Val Ser Ala Leu Glu Lys
1               5

<210> SEQ ID NO 8
<211> LENGTH: 7
<212> TYPE: PRT
<213> ORGANISM: Artificial Sequence
<220> FEATURE:
<223> OTHER INFORMATION: Motif

<400> SEQUENCE: 8

Lys Val Ser Ala Leu Lys Glu
1               5

<210> SEQ ID NO 9
<211> LENGTH: 21
<212> TYPE: PRT
<213> ORGANISM: Artificial Sequence
<220> FEATURE:
<223> OTHER INFORMATION: Motif

<400> SEQUENCE: 9

Glu Ile Ala Ala Leu Glu Lys Glu Ile Ala Ala Leu Glu Lys Glu Ile
1               5                   10                  15

Ala Ala Leu Glu Lys
            20

<210> SEQ ID NO 10
<211> LENGTH: 22
<212> TYPE: PRT
<213> ORGANISM: Artificial Sequence
<220> FEATURE:
<223> OTHER INFORMATION: Motif

<400> SEQUENCE: 10

Glu Ile Ala Ala Leu Glu Lys Glu Ile Ala Ala Leu Glu Lys Glu Ile
1               5                   10                  15

Ala Ala Leu Glu Lys Ala
            20

<210> SEQ ID NO 11
<211> LENGTH: 28
<212> TYPE: PRT
<213> ORGANISM: Artificial Sequence
<220> FEATURE:
<223> OTHER INFORMATION: Motif

<400> SEQUENCE: 11

Glu Ile Ala Ala Leu Glu Lys Glu Ile Ala Ala Leu Glu Lys Glu Ile
1               5                   10                  15

Ala Ala Leu Glu Lys Glu Ile Ala Ala Leu Glu Lys
            20                  25
```

<210> SEQ ID NO 12
<211> LENGTH: 29
<212> TYPE: PRT
<213> ORGANISM: Artificial Sequence
<220> FEATURE:
<223> OTHER INFORMATION: Motif

<400> SEQUENCE: 12

Glu Ile Ala Ala Leu Glu Lys Glu Ile Ala Ala Leu Glu Lys Glu Ile
1               5                   10                  15

Ala Ala Leu Glu Lys Glu Ile Ala Ala Leu Glu Lys Ala
            20                  25

<210> SEQ ID NO 13
<211> LENGTH: 21
<212> TYPE: PRT
<213> ORGANISM: Artificial Sequence
<220> FEATURE:
<223> OTHER INFORMATION: Motif

<400> SEQUENCE: 13

Lys Ile Ala Ala Leu Lys Glu Lys Ile Ala Ala Leu Lys Glu Lys Ile
1               5                   10                  15

Ala Ala Leu Lys Glu
            20

<210> SEQ ID NO 14
<211> LENGTH: 22
<212> TYPE: PRT
<213> ORGANISM: Artificial Sequence
<220> FEATURE:
<223> OTHER INFORMATION: Motif

<400> SEQUENCE: 14

Ala Lys Ile Ala Ala Leu Lys Glu Lys Ile Ala Ala Leu Lys Glu Lys
1               5                   10                  15

Ile Ala Ala Leu Lys Glu
            20

<210> SEQ ID NO 15
<211> LENGTH: 28
<212> TYPE: PRT
<213> ORGANISM: Artificial Sequence
<220> FEATURE:
<223> OTHER INFORMATION: Motif

<400> SEQUENCE: 15

Lys Ile Ala Ala Leu Lys Glu Lys Ile Ala Ala Leu Lys Glu Lys Ile
1               5                   10                  15

Ala Ala Leu Lys Glu Lys Ile Ala Ala Leu Lys Glu
            20                  25

<210> SEQ ID NO 16
<211> LENGTH: 29
<212> TYPE: PRT
<213> ORGANISM: Artificial Sequence
<220> FEATURE:
<223> OTHER INFORMATION: Motif

<400> SEQUENCE: 16

Ala Lys Ile Ala Ala Leu Lys Glu Lys Ile Ala Ala Leu Lys Glu Lys
1               5                   10                  15

Ile Ala Ala Leu Lys Glu Lys Ile Ala Ala Leu Lys Glu

```
                    20                  25

<210> SEQ ID NO 17
<211> LENGTH: 21
<212> TYPE: PRT
<213> ORGANISM: Artificial Sequence
<220> FEATURE:
<223> OTHER INFORMATION: Motif

<400> SEQUENCE: 17

Glu Ile Ser Ala Leu Glu Lys Glu Ile Ser Ala Leu Glu Lys Glu Ile
1               5                   10                  15

Ser Ala Leu Glu Lys
            20

<210> SEQ ID NO 18
<211> LENGTH: 22
<212> TYPE: PRT
<213> ORGANISM: Artificial Sequence
<220> FEATURE:
<223> OTHER INFORMATION: Motif

<400> SEQUENCE: 18

Glu Ile Ser Ala Leu Glu Lys Glu Ile Ser Ala Leu Glu Lys Glu Ile
1               5                   10                  15

Ser Ala Leu Glu Lys Ala
            20

<210> SEQ ID NO 19
<211> LENGTH: 28
<212> TYPE: PRT
<213> ORGANISM: Artificial Sequence
<220> FEATURE:
<223> OTHER INFORMATION: Motif

<400> SEQUENCE: 19

Glu Ile Ser Ala Leu Glu Lys Glu Ile Ser Ala Leu Glu Lys Glu Ile
1               5                   10                  15

Ser Ala Leu Glu Lys Glu Ile Ser Ala Leu Glu Lys
            20                  25

<210> SEQ ID NO 20
<211> LENGTH: 29
<212> TYPE: PRT
<213> ORGANISM: Artificial Sequence
<220> FEATURE:
<223> OTHER INFORMATION: Motif

<400> SEQUENCE: 20

Glu Ile Ser Ala Leu Glu Lys Glu Ile Ser Ala Leu Glu Lys Glu Ile
1               5                   10                  15

Ser Ala Leu Glu Lys Glu Ile Ser Ala Leu Glu Lys Ala
            20                  25

<210> SEQ ID NO 21
<211> LENGTH: 21
<212> TYPE: PRT
<213> ORGANISM: Artificial Sequence
<220> FEATURE:
<223> OTHER INFORMATION: Motif

<400> SEQUENCE: 21

Lys Ile Ser Ala Leu Lys Glu Lys Ile Ser Ala Leu Lys Glu Lys Ile
1               5                   10                  15
```

Ser Ala Leu Lys Glu
        20

<210> SEQ ID NO 22
<211> LENGTH: 22
<212> TYPE: PRT
<213> ORGANISM: Artificial Sequence
<220> FEATURE:
<223> OTHER INFORMATION: Motif

<400> SEQUENCE: 22

Ala Lys Ile Ser Ala Leu Lys Glu Lys Ile Ser Ala Leu Lys Glu Lys
1               5                   10                  15

Ile Ser Ala Leu Lys Glu
        20

<210> SEQ ID NO 23
<211> LENGTH: 28
<212> TYPE: PRT
<213> ORGANISM: Artificial Sequence
<220> FEATURE:
<223> OTHER INFORMATION: Motif

<400> SEQUENCE: 23

Lys Ile Ser Ala Leu Lys Glu Lys Ile Ser Ala Leu Lys Glu Lys Ile
1               5                   10                  15

Ser Ala Leu Lys Glu Lys Ile Ser Ala Leu Lys Glu
        20                  25

<210> SEQ ID NO 24
<211> LENGTH: 29
<212> TYPE: PRT
<213> ORGANISM: Artificial Sequence
<220> FEATURE:
<223> OTHER INFORMATION: Motif

<400> SEQUENCE: 24

Ala Lys Ile Ser Ala Leu Lys Glu Lys Ile Ser Ala Leu Lys Glu Lys
1               5                   10                  15

Ile Ser Ala Leu Lys Glu Lys Ile Ser Ala Leu Lys Glu
        20                  25

<210> SEQ ID NO 25
<211> LENGTH: 21
<212> TYPE: PRT
<213> ORGANISM: Artificial Sequence
<220> FEATURE:
<223> OTHER INFORMATION: Motif

<400> SEQUENCE: 25

Glu Val Ala Ala Leu Glu Lys Glu Val Ala Ala Leu Glu Lys Glu Val
1               5                   10                  15

Ala Ala Leu Glu Lys
        20

<210> SEQ ID NO 26
<211> LENGTH: 22
<212> TYPE: PRT
<213> ORGANISM: Artificial Sequence
<220> FEATURE:
<223> OTHER INFORMATION: Motif

<400> SEQUENCE: 26

Glu Val Ala Ala Leu Glu Lys Glu Val Ala Ala Leu Glu Lys Glu Val
1               5                   10                  15

Ala Ala Leu Glu Lys Ala
        20

<210> SEQ ID NO 27
<211> LENGTH: 28
<212> TYPE: PRT
<213> ORGANISM: Artificial Sequence
<220> FEATURE:
<223> OTHER INFORMATION: Motif

<400> SEQUENCE: 27

Glu Val Ala Ala Leu Glu Lys Glu Val Ala Ala Leu Glu Lys Glu Val
1               5                   10                  15

Ala Ala Leu Glu Lys Glu Val Ala Ala Leu Glu Lys
        20                  25

<210> SEQ ID NO 28
<211> LENGTH: 29
<212> TYPE: PRT
<213> ORGANISM: Artificial Sequence
<220> FEATURE:
<223> OTHER INFORMATION: Motif

<400> SEQUENCE: 28

Glu Val Ala Ala Leu Glu Lys Glu Val Ala Ala Leu Glu Lys Glu Val
1               5                   10                  15

Ala Ala Leu Glu Lys Glu Val Ala Ala Leu Glu Lys Ala
        20                  25

<210> SEQ ID NO 29
<211> LENGTH: 21
<212> TYPE: PRT
<213> ORGANISM: Artificial Sequence
<220> FEATURE:
<223> OTHER INFORMATION: Motif

<400> SEQUENCE: 29

Lys Val Ala Ala Leu Lys Glu Lys Val Ala Ala Leu Lys Glu Lys Val
1               5                   10                  15

Ala Ala Leu Lys Glu
        20

<210> SEQ ID NO 30
<211> LENGTH: 22
<212> TYPE: PRT
<213> ORGANISM: Artificial Sequence
<220> FEATURE:
<223> OTHER INFORMATION: Motif

<400> SEQUENCE: 30

Ala Lys Val Ala Ala Leu Lys Glu Lys Val Ala Ala Leu Lys Glu Lys
1               5                   10                  15

Val Ala Ala Leu Lys Glu
        20

<210> SEQ ID NO 31
<211> LENGTH: 28
<212> TYPE: PRT
<213> ORGANISM: Artificial Sequence
<220> FEATURE:
<223> OTHER INFORMATION: Motif

<400> SEQUENCE: 31

Lys Val Ala Ala Leu Lys Glu Lys Val Ala Ala Leu Lys Glu Lys Val

```
                1               5                  10                 15
Ala Ala Leu Lys Glu Lys Val Ala Ala Leu Lys Glu
            20                  25

<210> SEQ ID NO 32
<211> LENGTH: 29
<212> TYPE: PRT
<213> ORGANISM: Artificial Sequence
<220> FEATURE:
<223> OTHER INFORMATION: Motif

<400> SEQUENCE: 32

Ala Lys Val Ala Ala Leu Lys Glu Lys Val Ala Ala Leu Lys Glu Lys
1               5                   10                  15

Val Ala Ala Leu Lys Glu Lys Val Ala Ala Leu Lys Glu
            20                  25

<210> SEQ ID NO 33
<211> LENGTH: 21
<212> TYPE: PRT
<213> ORGANISM: Artificial Sequence
<220> FEATURE:
<223> OTHER INFORMATION: Motif

<400> SEQUENCE: 33

Glu Val Ser Ala Leu Glu Lys Glu Val Ser Ala Leu Glu Lys Glu Val
1               5                   10                  15

Ser Ala Leu Glu Lys
            20

<210> SEQ ID NO 34
<211> LENGTH: 22
<212> TYPE: PRT
<213> ORGANISM: Artificial Sequence
<220> FEATURE:
<223> OTHER INFORMATION: Motif

<400> SEQUENCE: 34

Glu Val Ser Ala Leu Glu Lys Glu Val Ser Ala Leu Glu Lys Glu Val
1               5                   10                  15

Ser Ala Leu Glu Lys Ala
            20

<210> SEQ ID NO 35
<211> LENGTH: 28
<212> TYPE: PRT
<213> ORGANISM: Artificial Sequence
<220> FEATURE:
<223> OTHER INFORMATION: Motif

<400> SEQUENCE: 35

Glu Val Ser Ala Leu Glu Lys Glu Val Ser Ala Leu Glu Lys Glu Val
1               5                   10                  15

Ser Ala Leu Glu Lys Glu Val Ser Ala Leu Glu Lys
            20                  25

<210> SEQ ID NO 36
<211> LENGTH: 29
<212> TYPE: PRT
<213> ORGANISM: Artificial Sequence
<220> FEATURE:
<223> OTHER INFORMATION: Motif

<400> SEQUENCE: 36
```

-continued

Glu Val Ser Ala Leu Glu Lys Glu Val Ser Ala Leu Glu Lys Glu Val
1               5                   10                  15

Ser Ala Leu Glu Lys Glu Val Ser Ala Leu Glu Lys Ala
            20                  25

<210> SEQ ID NO 37
<211> LENGTH: 21
<212> TYPE: PRT
<213> ORGANISM: Artificial Sequence
<220> FEATURE:
<223> OTHER INFORMATION: Motif

<400> SEQUENCE: 37

Lys Val Ser Ala Leu Lys Glu Lys Val Ser Ala Leu Lys Glu Lys Val
1               5                   10                  15

Ser Ala Leu Lys Glu
            20

<210> SEQ ID NO 38
<211> LENGTH: 22
<212> TYPE: PRT
<213> ORGANISM: Artificial Sequence
<220> FEATURE:
<223> OTHER INFORMATION: Motif

<400> SEQUENCE: 38

Ala Lys Val Ser Ala Leu Lys Glu Lys Val Ser Ala Leu Lys Glu Lys
1               5                   10                  15

Val Ser Ala Leu Lys Glu
            20

<210> SEQ ID NO 39
<211> LENGTH: 28
<212> TYPE: PRT
<213> ORGANISM: Artificial Sequence
<220> FEATURE:
<223> OTHER INFORMATION: Motif

<400> SEQUENCE: 39

Lys Val Ser Ala Leu Lys Glu Lys Val Ser Ala Leu Lys Glu Lys Val
1               5                   10                  15

Ser Ala Leu Lys Glu Lys Val Ser Ala Leu Lys Glu
            20                  25

<210> SEQ ID NO 40
<211> LENGTH: 29
<212> TYPE: PRT
<213> ORGANISM: Artificial Sequence
<220> FEATURE:
<223> OTHER INFORMATION: Motif

<400> SEQUENCE: 40

Ala Lys Val Ser Ala Leu Lys Glu Lys Val Ser Ala Leu Lys Glu Lys
1               5                   10                  15

Val Ser Ala Leu Lys Glu Lys Val Ser Ala Leu Lys Glu
            20                  25

<210> SEQ ID NO 41
<211> LENGTH: 8
<212> TYPE: PRT
<213> ORGANISM: Artificial Sequence
<220> FEATURE:
<223> OTHER INFORMATION: C-terminal motif

<400> SEQUENCE: 41

Glu Ile Ala Ala Leu Glu Lys Ala
1               5

<210> SEQ ID NO 42
<211> LENGTH: 8
<212> TYPE: PRT
<213> ORGANISM: Artificial Sequence
<220> FEATURE:
<223> OTHER INFORMATION: N-terminal motif

<400> SEQUENCE: 42

Ala Lys Ile Ala Ala Leu Lys Glu
1               5

<210> SEQ ID NO 43
<211> LENGTH: 8
<212> TYPE: PRT
<213> ORGANISM: Artificial Sequence
<220> FEATURE:
<223> OTHER INFORMATION: C-terminal motif

<400> SEQUENCE: 43

Glu Ile Ser Ala Leu Glu Lys Ala
1               5

<210> SEQ ID NO 44
<211> LENGTH: 8
<212> TYPE: PRT
<213> ORGANISM: Artificial Sequence
<220> FEATURE:
<223> OTHER INFORMATION: N-terminal motif

<400> SEQUENCE: 44

Ala Lys Ile Ser Ala Leu Lys Glu
1               5

<210> SEQ ID NO 45
<211> LENGTH: 8
<212> TYPE: PRT
<213> ORGANISM: Artificial Sequence
<220> FEATURE:
<223> OTHER INFORMATION: C-terminal motif

<400> SEQUENCE: 45

Glu Val Ala Ala Leu Glu Lys Ala
1               5

<210> SEQ ID NO 46
<211> LENGTH: 8
<212> TYPE: PRT
<213> ORGANISM: Artificial Sequence
<220> FEATURE:
<223> OTHER INFORMATION: N-terminal motif

<400> SEQUENCE: 46

Ala Lys Val Ala Ala Leu Lys Glu
1               5

<210> SEQ ID NO 47
<211> LENGTH: 8
<212> TYPE: PRT
<213> ORGANISM: Artificial Sequence
<220> FEATURE:
<223> OTHER INFORMATION: C-terminal motif

<400> SEQUENCE: 47

Glu Val Ser Ala Leu Glu Lys Ala
1               5

<210> SEQ ID NO 48
<211> LENGTH: 8
<212> TYPE: PRT
<213> ORGANISM: Artificial Sequence
<220> FEATURE:
<223> OTHER INFORMATION: N-terminal motif

<400> SEQUENCE: 48

Ala Lys Val Ser Ala Leu Lys Glu
1               5

<210> SEQ ID NO 49
<211> LENGTH: 289
<212> TYPE: PRT
<213> ORGANISM: Artificial Sequence
<220> FEATURE:
<223> OTHER INFORMATION: scFv-coil1

<400> SEQUENCE: 49

Glu Val Gln Leu Gln Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Leu Asn Thr Tyr Thr Gly Glu Ser Ile Tyr Pro Asp Asp Phe
    50                  55                  60

Lys Gly Arg Phe Ala Phe Ser Ser Glu Thr Ser Ala Ser Thr Ala Tyr
65                  70                  75                  80

Leu Gln Ile Asn Asn Leu Lys Asn Glu Asp Met Ala Thr Tyr Phe Cys
                85                  90                  95

Ala Arg Gly Asp Tyr Gly Tyr Asp Asp Pro Leu Asp Tyr Trp Gly Gln
            100                 105                 110

Gly Thr Ser Val Thr Val Ser Ser Gly Gly Gly Gly Ser Gly Gly Gly
        115                 120                 125

Gly Ser Gly Gly Gly Gly Ser Asp Ile Val Met Thr Gln Ala Ala Pro
    130                 135                 140

Ser Val Pro Val Thr Pro Gly Glu Ser Val Ser Ile Ser Cys Arg Ser
145                 150                 155                 160

Ser Lys Ser Leu Leu His Thr Asn Gly Asn Thr Tyr Leu His Trp Phe
                165                 170                 175

Leu Gln Arg Pro Gly Gln Ser Pro Gln Leu Leu Ile Tyr Arg Met Ser
            180                 185                 190

Val Leu Ala Ser Gly Val Pro Asp Arg Phe Ser Gly Ser Gly Ser Gly
        195                 200                 205

Thr Ala Phe Thr Leu Ser Ile Ser Arg Val Glu Ala Glu Asp Val Gly
    210                 215                 220

Val Phe Tyr Cys Met Gln His Leu Glu Tyr Pro Leu Thr Phe Gly Ala
225                 230                 235                 240

Gly Thr Lys Leu Glu Leu Lys Gly Gly Ser Lys Gly Pro Glu Val
                245                 250                 255

Ser Ala Leu Glu Lys Glu Val Ser Ala Leu Glu Lys Glu Val Ser Ala
                260                 265                 270

Leu Glu Lys Glu Val Ser Ala Leu Glu Lys Glu Val Ser Ala Leu Glu
            275                 280                 285

Lys

<210> SEQ ID NO 50
<211> LENGTH: 290
<212> TYPE: PRT
<213> ORGANISM: Artificial Sequence
<220> FEATURE:
<223> OTHER INFORMATION: scFv-coil1ala

<400> SEQUENCE: 50

```
Glu Val Gln Leu Gln Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Leu Asn Thr Tyr Thr Gly Glu Ser Ile Tyr Pro Asp Asp Phe
    50                  55                  60

Lys Gly Arg Phe Ala Phe Ser Ser Glu Thr Ser Ala Ser Thr Ala Tyr
65                  70                  75                  80

Leu Gln Ile Asn Asn Leu Lys Asn Glu Asp Met Ala Thr Tyr Phe Cys
                85                  90                  95

Ala Arg Gly Asp Tyr Gly Tyr Asp Asp Pro Leu Asp Tyr Trp Gly Gln
            100                 105                 110

Gly Thr Ser Val Thr Val Ser Ser Gly Gly Gly Gly Ser Gly Gly Gly
        115                 120                 125

Gly Ser Gly Gly Gly Gly Ser Asp Ile Val Met Thr Gln Ala Ala Pro
    130                 135                 140

Ser Val Pro Val Thr Pro Gly Glu Ser Val Ser Ile Ser Cys Arg Ser
145                 150                 155                 160

Ser Lys Ser Leu Leu His Thr Asn Gly Asn Thr Tyr Leu His Trp Phe
                165                 170                 175

Leu Gln Arg Pro Gly Gln Ser Pro Gln Leu Leu Ile Tyr Arg Met Ser
            180                 185                 190

Val Leu Ala Ser Gly Val Pro Asp Arg Phe Ser Gly Ser Gly Ser Gly
        195                 200                 205

Thr Ala Phe Thr Leu Ser Ile Ser Arg Val Glu Ala Glu Asp Val Gly
    210                 215                 220

Val Phe Tyr Cys Met Gln His Leu Glu Tyr Pro Leu Thr Phe Gly Ala
225                 230                 235                 240

Gly Thr Lys Leu Glu Leu Lys Gly Gly Ser Lys Gly Pro Glu Val
                245                 250                 255

Ser Ala Leu Glu Lys Glu Val Ser Ala Leu Glu Lys Glu Val Ser Ala
            260                 265                 270

Leu Glu Lys Glu Val Ser Ala Leu Glu Lys Glu Val Ser Ala Leu Glu
        275                 280                 285

Lys Ala
    290
```

<210> SEQ ID NO 51
<211> LENGTH: 35
<212> TYPE: PRT
<213> ORGANISM: Artificial Sequence
<220> FEATURE:
<223> OTHER INFORMATION: pepK

<400> SEQUENCE: 51

```
Lys Val Ser Ala Leu Lys Glu Lys Val Ser Ala Leu Lys Glu Lys Val
1               5                   10                  15

Ser Ala Leu Lys Glu Lys Val Ser Ala Leu Lys Glu Lys Val Ser Ala
            20                  25                  30

Leu Lys Glu
        35
```

<210> SEQ ID NO 52
<211> LENGTH: 35
<212> TYPE: PRT
<213> ORGANISM: Artificial Sequence
<220> FEATURE:
<223> OTHER INFORMATION: Motif

<400> SEQUENCE: 52

```
Glu Ile Ala Ala Leu Glu Lys Glu Ile Ala Ala Leu Glu Lys Glu Ile
1               5                   10                  15

Ala Ala Leu Glu Lys Glu Ile Ala Ala Leu Glu Lys Glu Ile Ala Ala
            20                  25                  30

Leu Glu Lys
        35
```

<210> SEQ ID NO 53
<211> LENGTH: 36
<212> TYPE: PRT
<213> ORGANISM: Artificial Sequence
<220> FEATURE:
<223> OTHER INFORMATION: Motif

<400> SEQUENCE: 53

```
Glu Ile Ala Ala Leu Glu Lys Glu Ile Ala Ala Leu Glu Lys Glu Ile
1               5                   10                  15

Ala Ala Leu Glu Lys Glu Ile Ala Ala Leu Glu Lys Glu Ile Ala Ala
            20                  25                  30

Leu Glu Lys Ala
        35
```

<210> SEQ ID NO 54
<211> LENGTH: 35
<212> TYPE: PRT
<213> ORGANISM: Artificial Sequence
<220> FEATURE:
<223> OTHER INFORMATION: Motif

<400> SEQUENCE: 54

```
Lys Ile Ala Ala Leu Lys Glu Lys Ile Ala Ala Leu Lys Glu Lys Ile
1               5                   10                  15

Ala Ala Leu Lys Glu Lys Ile Ala Ala Leu Lys Glu Lys Ile Ala Ala
            20                  25                  30

Leu Lys Glu
        35
```

<210> SEQ ID NO 55
<211> LENGTH: 36
<212> TYPE: PRT
<213> ORGANISM: Artificial Sequence
<220> FEATURE:
<223> OTHER INFORMATION: Motif

<400> SEQUENCE: 55

```
Ala Lys Ile Ala Ala Leu Lys Glu Lys Ile Ala Ala Leu Lys Glu Lys
1               5                   10                  15
```

Ile Ala Ala Leu Lys Glu Lys Ile Ala Ala Leu Lys Glu Lys Ile Ala
            20                  25                  30

Ala Leu Lys Glu
        35

<210> SEQ ID NO 56
<211> LENGTH: 35
<212> TYPE: PRT
<213> ORGANISM: Artificial Sequence
<220> FEATURE:
<223> OTHER INFORMATION: Motif

<400> SEQUENCE: 56

Glu Ile Ser Ala Leu Glu Lys Glu Ile Ser Ala Leu Glu Lys Glu Ile
1               5                   10                  15

Ser Ala Leu Glu Lys Glu Ile Ser Ala Leu Glu Lys Glu Ile Ser Ala
            20                  25                  30

Leu Glu Lys
        35

<210> SEQ ID NO 57
<211> LENGTH: 36
<212> TYPE: PRT
<213> ORGANISM: Artificial Sequence
<220> FEATURE:
<223> OTHER INFORMATION: Motif

<400> SEQUENCE: 57

Glu Ile Ser Ala Leu Glu Lys Glu Ile Ser Ala Leu Glu Lys Glu Ile
1               5                   10                  15

Ser Ala Leu Glu Lys Glu Ile Ser Ala Leu Glu Lys Glu Ile Ser Ala
            20                  25                  30

Leu Glu Lys Ala
        35

<210> SEQ ID NO 58
<211> LENGTH: 35
<212> TYPE: PRT
<213> ORGANISM: Artificial Sequence
<220> FEATURE:
<223> OTHER INFORMATION: Motif

<400> SEQUENCE: 58

Lys Ile Ser Ala Leu Lys Glu Lys Ile Ser Ala Leu Lys Glu Lys Ile
1               5                   10                  15

Ser Ala Leu Lys Glu Lys Ile Ser Ala Leu Lys Glu Lys Ile Ser Ala
            20                  25                  30

Leu Lys Glu
        35

<210> SEQ ID NO 59
<211> LENGTH: 36
<212> TYPE: PRT
<213> ORGANISM: Artificial Sequence
<220> FEATURE:
<223> OTHER INFORMATION: Motif

<400> SEQUENCE: 59

Ala Lys Ile Ser Ala Leu Lys Glu Lys Ile Ser Ala Leu Lys Glu Lys
1               5                   10                  15

Ile Ser Ala Leu Lys Glu Lys Ile Ser Ala Leu Lys Glu Lys Ile Ser
            20                  25                  30

Ala Leu Lys Glu
        35

<210> SEQ ID NO 60
<211> LENGTH: 35
<212> TYPE: PRT
<213> ORGANISM: Artificial Sequence
<220> FEATURE:
<223> OTHER INFORMATION: Motif

<400> SEQUENCE: 60

Glu Val Ala Ala Leu Glu Lys Glu Val Ala Ala Leu Glu Lys Glu Val
1               5                   10                  15

Ala Ala Leu Glu Lys Glu Val Ala Ala Leu Glu Lys Glu Val Ala Ala
            20                  25                  30

Leu Glu Lys
        35

<210> SEQ ID NO 61
<211> LENGTH: 36
<212> TYPE: PRT
<213> ORGANISM: Artificial Sequence
<220> FEATURE:
<223> OTHER INFORMATION: Motif

<400> SEQUENCE: 61

Glu Val Ala Ala Leu Glu Lys Glu Val Ala Ala Leu Glu Lys Glu Val
1               5                   10                  15

Ala Ala Leu Glu Lys Glu Val Ala Ala Leu Glu Lys Glu Val Ala Ala
            20                  25                  30

Leu Glu Lys Ala
        35

<210> SEQ ID NO 62
<211> LENGTH: 35
<212> TYPE: PRT
<213> ORGANISM: Artificial Sequence
<220> FEATURE:
<223> OTHER INFORMATION: Motif

<400> SEQUENCE: 62

Lys Val Ala Ala Leu Lys Glu Lys Val Ala Ala Leu Lys Glu Lys Val
1               5                   10                  15

Ala Ala Leu Lys Glu Lys Val Ala Ala Leu Lys Glu Lys Val Ala Ala
            20                  25                  30

Leu Lys Glu
        35

<210> SEQ ID NO 63
<211> LENGTH: 36
<212> TYPE: PRT
<213> ORGANISM: Artificial Sequence
<220> FEATURE:
<223> OTHER INFORMATION: Motif

<400> SEQUENCE: 63

Ala Lys Val Ala Ala Leu Lys Glu Lys Val Ala Ala Leu Lys Glu Lys
1               5                   10                  15

Val Ala Ala Leu Lys Glu Lys Val Ala Ala Leu Lys Glu Lys Val Ala
            20                  25                  30

Ala Leu Lys Glu
        35

<210> SEQ ID NO 64
<211> LENGTH: 35
<212> TYPE: PRT
<213> ORGANISM: Artificial Sequence
<220> FEATURE:
<223> OTHER INFORMATION: Motif

<400> SEQUENCE: 64

Glu Val Ser Ala Leu Glu Lys Glu Val Ser Ala Leu Glu Lys Glu Val
1               5                   10                  15

Ser Ala Leu Glu Lys Glu Val Ser Ala Leu Glu Lys Glu Val Ser Ala
            20                  25                  30

Leu Glu Lys
        35

<210> SEQ ID NO 65
<211> LENGTH: 36
<212> TYPE: PRT
<213> ORGANISM: Artificial Sequence
<220> FEATURE:
<223> OTHER INFORMATION: Motif

<400> SEQUENCE: 65

Glu Val Ser Ala Leu Glu Lys Glu Val Ser Ala Leu Glu Lys Glu Val
1               5                   10                  15

Ser Ala Leu Glu Lys Glu Val Ser Ala Leu Glu Lys Glu Val Ser Ala
            20                  25                  30

Leu Glu Lys Ala
        35

<210> SEQ ID NO 66
<211> LENGTH: 35
<212> TYPE: PRT
<213> ORGANISM: Artificial Sequence
<220> FEATURE:
<223> OTHER INFORMATION: Motif

<400> SEQUENCE: 66

Lys Val Ser Ala Leu Lys Glu Lys Val Ser Ala Leu Lys Glu Lys Val
1               5                   10                  15

Ser Ala Leu Lys Glu Lys Val Ser Ala Leu Lys Glu Lys Val Ser Ala
            20                  25                  30

Leu Lys Glu
        35

<210> SEQ ID NO 67
<211> LENGTH: 36
<212> TYPE: PRT
<213> ORGANISM: Artificial Sequence
<220> FEATURE:
<223> OTHER INFORMATION: Motif

<400> SEQUENCE: 67

Ala Lys Val Ser Ala Leu Lys Glu Lys Val Ser Ala Leu Lys Glu Lys
1               5                   10                  15

Val Ser Ala Leu Lys Glu Lys Val Ser Ala Leu Lys Glu Lys Val Ser
            20                  25                  30

Ala Leu Lys Glu
        35

<210> SEQ ID NO 68

```
<211> LENGTH: 22
<212> TYPE: PRT
<213> ORGANISM: Artificial Sequence
<220> FEATURE:
<223> OTHER INFORMATION: Motif

<400> SEQUENCE: 68

Glu Ile Ala Ala Leu Glu Lys Glu Ile Ala Ala Leu Glu Lys Glu Ile
1               5                   10                  15
Ala Ala Leu Glu Lys Gly
            20

<210> SEQ ID NO 69
<211> LENGTH: 8
<212> TYPE: PRT
<213> ORGANISM: Artificial Sequence
<220> FEATURE:
<223> OTHER INFORMATION: Motif

<400> SEQUENCE: 69

Glu Ile Ala Ala Leu Glu Lys Gly
1               5

<210> SEQ ID NO 70
<211> LENGTH: 22
<212> TYPE: PRT
<213> ORGANISM: Artificial Sequence
<220> FEATURE:
<223> OTHER INFORMATION: Motif

<400> SEQUENCE: 70

Glu Ile Ala Ala Leu Glu Lys Glu Ile Ala Ala Leu Glu Lys Glu Ile
1               5                   10                  15
Ala Ala Leu Glu Lys Ser
            20

<210> SEQ ID NO 71
<211> LENGTH: 8
<212> TYPE: PRT
<213> ORGANISM: Artificial Sequence
<220> FEATURE:
<223> OTHER INFORMATION: Motif

<400> SEQUENCE: 71

Glu Ile Ala Ala Leu Glu Lys Ser
1               5

<210> SEQ ID NO 72
<211> LENGTH: 29
<212> TYPE: PRT
<213> ORGANISM: Artificial Sequence
<220> FEATURE:
<223> OTHER INFORMATION: Motif

<400> SEQUENCE: 72

Glu Ile Ala Ala Leu Glu Lys Glu Ile Ala Ala Leu Glu Lys Glu Ile
1               5                   10                  15
Ala Ala Leu Glu Lys Glu Ile Ala Ala Leu Glu Lys Gly
            20                  25

<210> SEQ ID NO 73
<211> LENGTH: 29
<212> TYPE: PRT
<213> ORGANISM: Artificial Sequence
<220> FEATURE:
<223> OTHER INFORMATION: Motif
```

<400> SEQUENCE: 73

Glu Ile Ala Ala Leu Glu Lys Glu Ile Ala Ala Leu Glu Lys Glu Ile
1               5                   10                  15

Ala Ala Leu Glu Lys Glu Ile Ala Ala Leu Glu Lys Ser
            20                  25

<210> SEQ ID NO 74
<211> LENGTH: 36
<212> TYPE: PRT
<213> ORGANISM: Artificial Sequence
<220> FEATURE:
<223> OTHER INFORMATION: Motif

<400> SEQUENCE: 74

Glu Ile Ala Ala Leu Glu Lys Glu Ile Ala Ala Leu Glu Lys Glu Ile
1               5                   10                  15

Ala Ala Leu Glu Lys Glu Ile Ala Ala Leu Glu Lys Glu Ile Ala Ala
            20                  25                  30

Leu Glu Lys Gly
        35

<210> SEQ ID NO 75
<211> LENGTH: 36
<212> TYPE: PRT
<213> ORGANISM: Artificial Sequence
<220> FEATURE:
<223> OTHER INFORMATION: Motif

<400> SEQUENCE: 75

Glu Ile Ala Ala Leu Glu Lys Glu Ile Ala Ala Leu Glu Lys Glu Ile
1               5                   10                  15

Ala Ala Leu Glu Lys Glu Ile Ala Ala Leu Glu Lys Glu Ile Ala Ala
            20                  25                  30

Leu Glu Lys Ser
        35

<210> SEQ ID NO 76
<211> LENGTH: 22
<212> TYPE: PRT
<213> ORGANISM: Artificial Sequence
<220> FEATURE:
<223> OTHER INFORMATION: Motif

<400> SEQUENCE: 76

Gly Lys Ile Ala Ala Leu Lys Glu Lys Ile Ala Ala Leu Lys Glu Lys
1               5                   10                  15

Ile Ala Ala Leu Lys Glu
            20

<210> SEQ ID NO 77
<211> LENGTH: 8
<212> TYPE: PRT
<213> ORGANISM: Artificial Sequence
<220> FEATURE:
<223> OTHER INFORMATION: Motif

<400> SEQUENCE: 77

Gly Lys Ile Ala Ala Leu Lys Glu
1               5

<210> SEQ ID NO 78
<211> LENGTH: 22

```
<212> TYPE: PRT
<213> ORGANISM: Artificial Sequence
<220> FEATURE:
<223> OTHER INFORMATION: Motif

<400> SEQUENCE: 78

Ser Lys Ile Ala Ala Leu Lys Glu Lys Ile Ala Ala Leu Lys Glu Lys
1               5                   10                  15

Ile Ala Ala Leu Lys Glu
            20

<210> SEQ ID NO 79
<211> LENGTH: 8
<212> TYPE: PRT
<213> ORGANISM: Artificial Sequence
<220> FEATURE:
<223> OTHER INFORMATION: Motif

<400> SEQUENCE: 79

Ser Lys Ile Ala Ala Leu Lys Glu
1               5

<210> SEQ ID NO 80
<211> LENGTH: 29
<212> TYPE: PRT
<213> ORGANISM: Artificial Sequence
<220> FEATURE:
<223> OTHER INFORMATION: Motif

<400> SEQUENCE: 80

Gly Lys Ile Ala Ala Leu Lys Glu Lys Ile Ala Ala Leu Lys Glu Lys
1               5                   10                  15

Ile Ala Ala Leu Lys Glu Lys Ile Ala Ala Leu Lys Glu
            20                  25

<210> SEQ ID NO 81
<211> LENGTH: 29
<212> TYPE: PRT
<213> ORGANISM: Artificial Sequence
<220> FEATURE:
<223> OTHER INFORMATION: Motif

<400> SEQUENCE: 81

Ser Lys Ile Ala Ala Leu Lys Glu Lys Ile Ala Ala Leu Lys Glu Lys
1               5                   10                  15

Ile Ala Ala Leu Lys Glu Lys Ile Ala Ala Leu Lys Glu
            20                  25

<210> SEQ ID NO 82
<211> LENGTH: 36
<212> TYPE: PRT
<213> ORGANISM: Artificial Sequence
<220> FEATURE:
<223> OTHER INFORMATION: Motif

<400> SEQUENCE: 82

Gly Lys Ile Ala Ala Leu Lys Glu Lys Ile Ala Ala Leu Lys Glu Lys
1               5                   10                  15

Ile Ala Ala Leu Lys Glu Lys Ile Ala Ala Leu Lys Glu Lys Ile Ala
            20                  25                  30

Ala Leu Lys Glu
        35

<210> SEQ ID NO 83
```

<211> LENGTH: 36
<212> TYPE: PRT
<213> ORGANISM: Artificial Sequence
<220> FEATURE:
<223> OTHER INFORMATION: Motif

<400> SEQUENCE: 83

Ser Lys Ile Ala Ala Leu Lys Glu Lys Ile Ala Ala Leu Lys Glu Lys
1               5                   10                  15
Ile Ala Ala Leu Lys Glu Lys Ile Ala Ala Leu Lys Glu Lys Ile Ala
            20                  25                  30
Ala Leu Lys Glu
        35

<210> SEQ ID NO 84
<211> LENGTH: 22
<212> TYPE: PRT
<213> ORGANISM: Artificial Sequence
<220> FEATURE:
<223> OTHER INFORMATION: Motif

<400> SEQUENCE: 84

Glu Ile Ser Ala Leu Glu Lys Glu Ile Ser Ala Leu Glu Lys Glu Ile
1               5                   10                  15
Ser Ala Leu Glu Lys Gly
            20

<210> SEQ ID NO 85
<211> LENGTH: 8
<212> TYPE: PRT
<213> ORGANISM: Artificial Sequence
<220> FEATURE:
<223> OTHER INFORMATION: Motif

<400> SEQUENCE: 85

Glu Ile Ser Ala Leu Glu Lys Gly
1               5

<210> SEQ ID NO 86
<211> LENGTH: 22
<212> TYPE: PRT
<213> ORGANISM: Artificial Sequence
<220> FEATURE:
<223> OTHER INFORMATION: Motif

<400> SEQUENCE: 86

Glu Ile Ser Ala Leu Glu Lys Glu Ile Ser Ala Leu Glu Lys Glu Ile
1               5                   10                  15
Ser Ala Leu Glu Lys Ser
            20

<210> SEQ ID NO 87
<211> LENGTH: 8
<212> TYPE: PRT
<213> ORGANISM: Artificial Sequence
<220> FEATURE:
<223> OTHER INFORMATION: Motif

<400> SEQUENCE: 87

Glu Ile Ser Ala Leu Glu Lys Ser
1               5

<210> SEQ ID NO 88
<211> LENGTH: 29
<212> TYPE: PRT

```
<213> ORGANISM: Artificial Sequence
<220> FEATURE:
<223> OTHER INFORMATION: Motif

<400> SEQUENCE: 88

Glu Ile Ser Ala Leu Glu Lys Glu Ile Ser Ala Leu Glu Lys Glu Ile
1               5                   10                  15
Ser Ala Leu Glu Lys Glu Ile Ser Ala Leu Glu Lys Gly
            20                  25

<210> SEQ ID NO 89
<211> LENGTH: 29
<212> TYPE: PRT
<213> ORGANISM: Artificial Sequence
<220> FEATURE:
<223> OTHER INFORMATION: Motif

<400> SEQUENCE: 89

Glu Ile Ser Ala Leu Glu Lys Glu Ile Ser Ala Leu Glu Lys Glu Ile
1               5                   10                  15
Ser Ala Leu Glu Lys Glu Ile Ser Ala Leu Glu Lys Ser
            20                  25

<210> SEQ ID NO 90
<211> LENGTH: 36
<212> TYPE: PRT
<213> ORGANISM: Artificial Sequence
<220> FEATURE:
<223> OTHER INFORMATION: Motif

<400> SEQUENCE: 90

Glu Ile Ser Ala Leu Glu Lys Glu Ile Ser Ala Leu Glu Lys Glu Ile
1               5                   10                  15
Ser Ala Leu Glu Lys Glu Ile Ser Ala Leu Glu Lys Glu Ile Ser Ala
            20                  25                  30
Leu Glu Lys Gly
        35

<210> SEQ ID NO 91
<211> LENGTH: 36
<212> TYPE: PRT
<213> ORGANISM: Artificial Sequence
<220> FEATURE:
<223> OTHER INFORMATION: Motif

<400> SEQUENCE: 91

Glu Ile Ser Ala Leu Glu Lys Glu Ile Ser Ala Leu Glu Lys Glu Ile
1               5                   10                  15
Ser Ala Leu Glu Lys Glu Ile Ser Ala Leu Glu Lys Glu Ile Ser Ala
            20                  25                  30
Leu Glu Lys Ser
        35

<210> SEQ ID NO 92
<211> LENGTH: 22
<212> TYPE: PRT
<213> ORGANISM: Artificial Sequence
<220> FEATURE:
<223> OTHER INFORMATION: Motif

<400> SEQUENCE: 92

Gly Lys Ile Ser Ala Leu Lys Glu Lys Ile Ser Ala Leu Lys Glu Lys
1               5                   10                  15
```

Ile Ser Ala Leu Lys Glu
            20

<210> SEQ ID NO 93
<211> LENGTH: 8
<212> TYPE: PRT
<213> ORGANISM: Artificial Sequence
<220> FEATURE:
<223> OTHER INFORMATION: Motif

<400> SEQUENCE: 93

Gly Lys Ile Ser Ala Leu Lys Glu
1               5

<210> SEQ ID NO 94
<211> LENGTH: 22
<212> TYPE: PRT
<213> ORGANISM: Artificial Sequence
<220> FEATURE:
<223> OTHER INFORMATION: Motif

<400> SEQUENCE: 94

Ser Lys Ile Ser Ala Leu Lys Glu Lys Ile Ser Ala Leu Lys Glu Lys
1               5                   10                  15

Ile Ser Ala Leu Lys Glu
            20

<210> SEQ ID NO 95
<211> LENGTH: 8
<212> TYPE: PRT
<213> ORGANISM: Artificial Sequence
<220> FEATURE:
<223> OTHER INFORMATION: Motif

<400> SEQUENCE: 95

Ser Lys Ile Ser Ala Leu Lys Glu
1               5

<210> SEQ ID NO 96
<211> LENGTH: 29
<212> TYPE: PRT
<213> ORGANISM: Artificial Sequence
<220> FEATURE:
<223> OTHER INFORMATION: Motif

<400> SEQUENCE: 96

Gly Lys Ile Ser Ala Leu Lys Glu Lys Ile Ser Ala Leu Lys Glu Lys
1               5                   10                  15

Ile Ser Ala Leu Lys Glu Lys Ile Ser Ala Leu Lys Glu
            20                  25

<210> SEQ ID NO 97
<211> LENGTH: 29
<212> TYPE: PRT
<213> ORGANISM: Artificial Sequence
<220> FEATURE:
<223> OTHER INFORMATION: Motif

<400> SEQUENCE: 97

Ser Lys Ile Ser Ala Leu Lys Glu Lys Ile Ser Ala Leu Lys Glu Lys
1               5                   10                  15

Ile Ser Ala Leu Lys Glu Lys Ile Ser Ala Leu Lys Glu
            20                  25

<210> SEQ ID NO 98

```
<211> LENGTH: 36
<212> TYPE: PRT
<213> ORGANISM: Artificial Sequence
<220> FEATURE:
<223> OTHER INFORMATION: Motif

<400> SEQUENCE: 98

Gly Lys Ile Ser Ala Leu Lys Glu Lys Ile Ser Ala Leu Lys Glu Lys
1               5                   10                  15

Ile Ser Ala Leu Lys Glu Lys Ile Ser Ala Leu Lys Glu Lys Ile Ser
            20                  25                  30

Ala Leu Lys Glu
        35

<210> SEQ ID NO 99
<211> LENGTH: 36
<212> TYPE: PRT
<213> ORGANISM: Artificial Sequence
<220> FEATURE:
<223> OTHER INFORMATION: Motif

<400> SEQUENCE: 99

Ser Lys Ile Ser Ala Leu Lys Glu Lys Ile Ser Ala Leu Lys Glu Lys
1               5                   10                  15

Ile Ser Ala Leu Lys Glu Lys Ile Ser Ala Leu Lys Glu Lys Ile Ser
            20                  25                  30

Ala Leu Lys Glu
        35

<210> SEQ ID NO 100
<211> LENGTH: 22
<212> TYPE: PRT
<213> ORGANISM: Artificial Sequence
<220> FEATURE:
<223> OTHER INFORMATION: Motif

<400> SEQUENCE: 100

Glu Val Ala Ala Leu Glu Lys Glu Val Ala Ala Leu Lys Glu Val
1               5                   10                  15

Ala Ala Leu Glu Lys Gly
            20

<210> SEQ ID NO 101
<211> LENGTH: 8
<212> TYPE: PRT
<213> ORGANISM: Artificial Sequence
<220> FEATURE:
<223> OTHER INFORMATION: Motif

<400> SEQUENCE: 101

Glu Val Ala Ala Leu Glu Lys Gly
1               5

<210> SEQ ID NO 102
<211> LENGTH: 22
<212> TYPE: PRT
<213> ORGANISM: Artificial Sequence
<220> FEATURE:
<223> OTHER INFORMATION: Motif

<400> SEQUENCE: 102

Glu Val Ala Ala Leu Glu Lys Glu Val Ala Ala Leu Glu Lys Glu Val
1               5                   10                  15

Ala Ala Leu Glu Lys Ser
```

20

<210> SEQ ID NO 103
<211> LENGTH: 8
<212> TYPE: PRT
<213> ORGANISM: Artificial Sequence
<220> FEATURE:
<223> OTHER INFORMATION: Motif

<400> SEQUENCE: 103

Glu Val Ala Ala Leu Glu Lys Ser
1               5

<210> SEQ ID NO 104
<211> LENGTH: 29
<212> TYPE: PRT
<213> ORGANISM: Artificial Sequence
<220> FEATURE:
<223> OTHER INFORMATION: Motif

<400> SEQUENCE: 104

Glu Val Ala Ala Leu Glu Lys Glu Val Ala Ala Leu Glu Lys Glu Val
1               5                  10                  15

Ala Ala Leu Glu Lys Glu Val Ala Ala Leu Glu Lys Gly
            20                  25

<210> SEQ ID NO 105
<211> LENGTH: 29
<212> TYPE: PRT
<213> ORGANISM: Artificial Sequence
<220> FEATURE:
<223> OTHER INFORMATION: Motif

<400> SEQUENCE: 105

Glu Val Ala Ala Leu Glu Lys Glu Val Ala Ala Leu Glu Lys Glu Val
1               5                  10                  15

Ala Ala Leu Glu Lys Glu Val Ala Ala Leu Glu Lys Ser
            20                  25

<210> SEQ ID NO 106
<211> LENGTH: 36
<212> TYPE: PRT
<213> ORGANISM: Artificial Sequence
<220> FEATURE:
<223> OTHER INFORMATION: Motif

<400> SEQUENCE: 106

Glu Val Ala Ala Leu Glu Lys Glu Val Ala Ala Leu Glu Lys Glu Val
1               5                  10                  15

Ala Ala Leu Glu Lys Glu Val Ala Ala Leu Glu Lys Glu Val Ala Ala
            20                  25                  30

Leu Glu Lys Gly
        35

<210> SEQ ID NO 107
<211> LENGTH: 36
<212> TYPE: PRT
<213> ORGANISM: Artificial Sequence
<220> FEATURE:
<223> OTHER INFORMATION: Motif

<400> SEQUENCE: 107

Glu Val Ala Ala Leu Glu Lys Glu Val Ala Ala Leu Glu Lys Glu Val
1               5                  10                  15

Ala Ala Leu Glu Lys Glu Val Ala Ala Leu Glu Lys Glu Val Ala Ala
            20                  25                  30

Leu Glu Lys Ser
        35

<210> SEQ ID NO 108
<211> LENGTH: 22
<212> TYPE: PRT
<213> ORGANISM: Artificial Sequence
<220> FEATURE:
<223> OTHER INFORMATION: Motif

<400> SEQUENCE: 108

Gly Lys Val Ala Ala Leu Lys Glu Lys Val Ala Ala Leu Lys Glu Lys
1               5                   10                  15

Val Ala Ala Leu Lys Glu
            20

<210> SEQ ID NO 109
<211> LENGTH: 8
<212> TYPE: PRT
<213> ORGANISM: Artificial Sequence
<220> FEATURE:
<223> OTHER INFORMATION: Motif

<400> SEQUENCE: 109

Gly Lys Val Ala Ala Leu Lys Glu
1               5

<210> SEQ ID NO 110
<211> LENGTH: 22
<212> TYPE: PRT
<213> ORGANISM: Artificial Sequence
<220> FEATURE:
<223> OTHER INFORMATION: Motif

<400> SEQUENCE: 110

Ser Lys Val Ala Ala Leu Lys Glu Lys Val Ala Ala Leu Lys Glu Lys
1               5                   10                  15

Val Ala Ala Leu Lys Glu
            20

<210> SEQ ID NO 111
<211> LENGTH: 8
<212> TYPE: PRT
<213> ORGANISM: Artificial Sequence
<220> FEATURE:
<223> OTHER INFORMATION: Motif

<400> SEQUENCE: 111

Ser Lys Val Ala Ala Leu Lys Glu
1               5

<210> SEQ ID NO 112
<211> LENGTH: 29
<212> TYPE: PRT
<213> ORGANISM: Artificial Sequence
<220> FEATURE:
<223> OTHER INFORMATION: Motif

<400> SEQUENCE: 112

Gly Lys Val Ala Ala Leu Lys Glu Lys Val Ala Ala Leu Lys Glu Lys
1               5                   10                  15

Val Ala Ala Leu Lys Glu Lys Val Ala Ala Leu Lys Glu
            20                  25

<210> SEQ ID NO 113
<211> LENGTH: 29
<212> TYPE: PRT
<213> ORGANISM: Artificial Sequence
<220> FEATURE:
<223> OTHER INFORMATION: Motif

<400> SEQUENCE: 113

Ser Lys Val Ala Ala Leu Lys Glu Lys Val Ala Ala Leu Lys Glu Lys
1               5                   10                  15

Val Ala Ala Leu Lys Glu Lys Val Ala Ala Leu Lys Glu
            20                  25

<210> SEQ ID NO 114
<211> LENGTH: 36
<212> TYPE: PRT
<213> ORGANISM: Artificial Sequence
<220> FEATURE:
<223> OTHER INFORMATION: Motif

<400> SEQUENCE: 114

Gly Lys Val Ala Ala Leu Lys Glu Lys Val Ala Ala Leu Lys Glu Lys
1               5                   10                  15

Val Ala Ala Leu Lys Glu Lys Val Ala Ala Leu Lys Glu Lys Val Ala
            20                  25                  30

Ala Leu Lys Glu
        35

<210> SEQ ID NO 115
<211> LENGTH: 36
<212> TYPE: PRT
<213> ORGANISM: Artificial Sequence
<220> FEATURE:
<223> OTHER INFORMATION: Motif

<400> SEQUENCE: 115

Ser Lys Val Ala Ala Leu Lys Glu Lys Val Ala Ala Leu Lys Glu Lys
1               5                   10                  15

Val Ala Ala Leu Lys Glu Lys Val Ala Ala Leu Lys Glu Lys Val Ala
            20                  25                  30

Ala Leu Lys Glu
        35

<210> SEQ ID NO 116
<211> LENGTH: 22
<212> TYPE: PRT
<213> ORGANISM: Artificial Sequence
<220> FEATURE:
<223> OTHER INFORMATION: Motif

<400> SEQUENCE: 116

Glu Val Ser Ala Leu Glu Lys Glu Val Ser Ala Leu Glu Lys Glu Val
1               5                   10                  15

Ser Ala Leu Glu Lys Gly
            20

<210> SEQ ID NO 117
<211> LENGTH: 8
<212> TYPE: PRT
<213> ORGANISM: Artificial Sequence
<220> FEATURE:
<223> OTHER INFORMATION: Motif

<400> SEQUENCE: 117

Glu Val Ser Ala Leu Glu Lys Gly
1               5

<210> SEQ ID NO 118
<211> LENGTH: 22
<212> TYPE: PRT
<213> ORGANISM: Artificial Sequence
<220> FEATURE:
<223> OTHER INFORMATION: Motif

<400> SEQUENCE: 118

Glu Val Ser Ala Leu Glu Lys Glu Val Ser Ala Leu Glu Lys Glu Val
1               5                   10                  15

Ser Ala Leu Glu Lys Ser
            20

<210> SEQ ID NO 119
<211> LENGTH: 8
<212> TYPE: PRT
<213> ORGANISM: Artificial Sequence
<220> FEATURE:
<223> OTHER INFORMATION: Motif

<400> SEQUENCE: 119

Glu Val Ser Ala Leu Glu Lys Ser
1               5

<210> SEQ ID NO 120
<211> LENGTH: 29
<212> TYPE: PRT
<213> ORGANISM: Artificial Sequence
<220> FEATURE:
<223> OTHER INFORMATION: Motif

<400> SEQUENCE: 120

Glu Val Ser Ala Leu Glu Lys Glu Val Ser Ala Leu Glu Lys Glu Val
1               5                   10                  15

Ser Ala Leu Glu Lys Glu Val Ser Ala Leu Glu Lys Gly
            20                  25

<210> SEQ ID NO 121
<211> LENGTH: 29
<212> TYPE: PRT
<213> ORGANISM: Artificial Sequence
<220> FEATURE:
<223> OTHER INFORMATION: Motif

<400> SEQUENCE: 121

Glu Val Ser Ala Leu Glu Lys Glu Val Ser Ala Leu Glu Lys Glu Val
1               5                   10                  15

Ser Ala Leu Glu Lys Glu Val Ser Ala Leu Glu Lys Ser
            20                  25

<210> SEQ ID NO 122
<211> LENGTH: 36
<212> TYPE: PRT
<213> ORGANISM: Artificial Sequence
<220> FEATURE:
<223> OTHER INFORMATION: Motif

<400> SEQUENCE: 122

Glu Val Ser Ala Leu Glu Lys Glu Val Ser Ala Leu Glu Lys Glu Val
1               5                   10                  15

```
Ser Ala Leu Glu Lys Glu Val Ser Ala Leu Glu Lys Glu Val Ser Ala
            20                  25                  30

Leu Glu Lys Gly
        35

<210> SEQ ID NO 123
<211> LENGTH: 36
<212> TYPE: PRT
<213> ORGANISM: Artificial Sequence
<220> FEATURE:
<223> OTHER INFORMATION: Motif

<400> SEQUENCE: 123

Glu Val Ser Ala Leu Glu Lys Glu Val Ser Ala Leu Glu Lys Glu Val
1               5                   10                  15

Ser Ala Leu Glu Lys Glu Val Ser Ala Leu Glu Lys Glu Val Ser Ala
            20                  25                  30

Leu Glu Lys Ser
        35

<210> SEQ ID NO 124
<211> LENGTH: 22
<212> TYPE: PRT
<213> ORGANISM: Artificial Sequence
<220> FEATURE:
<223> OTHER INFORMATION: Motif

<400> SEQUENCE: 124

Gly Lys Val Ser Ala Leu Lys Glu Lys Val Ser Ala Leu Lys Glu Lys
1               5                   10                  15

Val Ser Ala Leu Lys Glu
            20

<210> SEQ ID NO 125
<211> LENGTH: 8
<212> TYPE: PRT
<213> ORGANISM: Artificial Sequence
<220> FEATURE:
<223> OTHER INFORMATION: Motif

<400> SEQUENCE: 125

Gly Lys Val Ser Ala Leu Lys Glu
1               5

<210> SEQ ID NO 126
<211> LENGTH: 22
<212> TYPE: PRT
<213> ORGANISM: Artificial Sequence
<220> FEATURE:
<223> OTHER INFORMATION: Motif

<400> SEQUENCE: 126

Ser Lys Val Ser Ala Leu Lys Glu Lys Val Ser Ala Leu Lys Glu Lys
1               5                   10                  15

Val Ser Ala Leu Lys Glu
            20

<210> SEQ ID NO 127
<211> LENGTH: 8
<212> TYPE: PRT
<213> ORGANISM: Artificial Sequence
<220> FEATURE:
<223> OTHER INFORMATION: Motif

<400> SEQUENCE: 127
```

Ser Lys Val Ser Ala Leu Lys Glu
1               5

<210> SEQ ID NO 128
<211> LENGTH: 29
<212> TYPE: PRT
<213> ORGANISM: Artificial Sequence
<220> FEATURE:
<223> OTHER INFORMATION: Motif

<400> SEQUENCE: 128

Gly Lys Val Ser Ala Leu Lys Glu Lys Val Ser Ala Leu Lys Glu Lys
1               5                   10                  15

Val Ser Ala Leu Lys Glu Lys Val Ser Ala Leu Lys Glu
            20                  25

<210> SEQ ID NO 129
<211> LENGTH: 29
<212> TYPE: PRT
<213> ORGANISM: Artificial Sequence
<220> FEATURE:
<223> OTHER INFORMATION: Motif

<400> SEQUENCE: 129

Ser Lys Val Ser Ala Leu Lys Glu Lys Val Ser Ala Leu Lys Glu Lys
1               5                   10                  15

Val Ser Ala Leu Lys Glu Lys Val Ser Ala Leu Lys Glu
            20                  25

<210> SEQ ID NO 130
<211> LENGTH: 36
<212> TYPE: PRT
<213> ORGANISM: Artificial Sequence
<220> FEATURE:
<223> OTHER INFORMATION: Motif

<400> SEQUENCE: 130

Gly Lys Val Ser Ala Leu Lys Glu Lys Val Ser Ala Leu Lys Glu Lys
1               5                   10                  15

Val Ser Ala Leu Lys Glu Lys Val Ser Ala Leu Lys Glu Lys Val Ser
            20                  25                  30

Ala Leu Lys Glu
        35

<210> SEQ ID NO 131
<211> LENGTH: 36
<212> TYPE: PRT
<213> ORGANISM: Artificial Sequence
<220> FEATURE:
<223> OTHER INFORMATION: Motif

<400> SEQUENCE: 131

Ser Lys Val Ser Ala Leu Lys Glu Lys Val Ser Ala Leu Lys Glu Lys
1               5                   10                  15

Val Ser Ala Leu Lys Glu Lys Val Ser Ala Leu Lys Glu Lys Val Ser
            20                  25                  30

Ala Leu Lys Glu
        35